(12) United States Patent
Pecora

(10) Patent No.: US 10,902,953 B2
(45) Date of Patent: *Jan. 26, 2021

(54) CLINICAL OUTCOME TRACKING AND ANALYSIS

(71) Applicant: COTA, Inc., New York, NY (US)

(72) Inventor: Andrew Pecora, Rumson, NJ (US)

(73) Assignee: COTA, Inc., New York, NY (US)

(*) Notice: Subject to any disclaimer, the term of this patent is extended or adjusted under 35 U.S.C. 154(b) by 210 days.

This patent is subject to a terminal disclaimer.

(21) Appl. No.: 15/894,618

(22) Filed: Feb. 12, 2018

(65) Prior Publication Data

US 2018/0174688 A1 Jun. 21, 2018

Related U.S. Application Data

(63) Continuation of application No. 14/507,640, filed on Oct. 6, 2014, now abandoned.
(Continued)

(51) Int. Cl.
*G16H 50/70* (2018.01)
*G06F 19/00* (2018.01)
(Continued)

(52) U.S. Cl.
CPC ........... *G16H 50/70* (2018.01); *G06F 16/285* (2019.01); *G06F 16/9024* (2019.01);
(Continued)

(58) Field of Classification Search
CPC ........ G06Q 30/02; G06Q 10/00; G06Q 10/06; G06Q 50/22–24; G06F 19/00; G06F 19/325; G06F 19/328
See application file for complete search history.

(56) References Cited

U.S. PATENT DOCUMENTS 6,699,193 B2 3/2004 Crutchfield et al.
7,774,377 B2 8/2010 Schoenberg
(Continued)

FOREIGN PATENT DOCUMENTS

JP 2003-310557 A 11/2003
JP 2004-133826 A 4/2004
(Continued)

*Primary Examiner* — Robert W Morgan
*Assistant Examiner* — Edward B Winston, III
(74) *Attorney, Agent, or Firm* — McCarter & English, LLP; Beverly W. Lubit

(57) ABSTRACT

The described invention provides a system and method for clinical outcome tracking and analysis. The clinical outcome tracking and analysis comprises sorting, outcome tracking, quality of life metrics, toxicity to therapy and cost of care. The system and method includes receiving one or more parameters. Exemplary parameters for sorting include sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care. A plurality of patient medical records are sorted, by a clinical outcome tracking and analysis module executed by a processor, to provide a set of patient medical records satisfying the one or more parameters. A nodal address, indicating one or more variables, is applied to the sorted set of patient medical records to determine a clinically relevant set of patient medical records as the sorted set of patient medical records satisfying the one or more variables. The clinically relevant set of patient medical records is analyzed. A communication is transmitted based on the analyzing to a user to effect treatment, to monitor performance, or to reduce at least one of treatment variability, waste or inefficiency while delivering on intended outcome.

43 Claims, 33 Drawing Sheets

Related U.S. Application Data

(60) Provisional application No. 61/888,418, filed on Oct. 8, 2013.

(51) Int. Cl.

| | | |
|---|---|---|
| *G06F 16/28* | (2019.01) | |
| *G06F 16/901* | (2019.01) | |
| *G06F 16/9535* | (2019.01) | |
| *G16H 10/20* | (2018.01) | |
| *G16H 40/63* | (2018.01) | |
| *G16H 10/60* | (2018.01) | |
| *G16H 50/20* | (2018.01) | |
| *G06Q 10/06* | (2012.01) | |
| *G06Q 30/02* | (2012.01) | |
| *G06Q 50/24* | (2012.01) | |
| *G16H 40/20* | (2018.01) | |

(52) U.S. Cl.
CPC ........ *G06F 16/9535* (2019.01); *G06F 19/325* (2013.01); *G06F 19/328* (2013.01); *G06F 19/36* (2013.01); *G06Q 10/0637* (2013.01); *G06Q 30/0201* (2013.01); *G06Q 50/24* (2013.01); *G16H 10/20* (2018.01); *G16H 10/60* (2018.01); *G16H 40/20* (2018.01); *G16H 40/63* (2018.01); *G16H 50/20* (2018.01)

(56) References Cited

U.S. PATENT DOCUMENTS

| | | |
|---|---|---|
| 8,019,552 B2 | 9/2011 | Dai et al. |
| 8,731,648 B2 | 5/2014 | Bardy |
| 2008/0033894 A1 | 2/2008 | Steck et al. |
| 2008/0091472 A1 | 4/2008 | Hoppe |
| 2008/0312959 A1* | 12/2008 | Rose ............... G16H 50/20 705/2 |
| 2009/0204430 A1 | 8/2009 | Gliklich |
| 2012/0029939 A1 | 2/2012 | Danielson et al. |
| 2012/0053425 A1* | 3/2012 | Michelson ......... G06Q 10/00 600/300 |
| 2012/0130737 A1* | 5/2012 | Finizio ............. G16H 15/00 705/2 |
| 2012/0166218 A1 | 6/2012 | Reiner |
| 2012/0271612 A1* | 10/2012 | Barsoum ............. G06F 19/00 703/11 |
| 2013/0226612 A1 | 8/2013 | Carmeli et al. |
| 2014/0006044 A1 | 1/2014 | Pradhan et al. |
| 2014/0244277 A1 | 8/2014 | Krishna Rao et al. |

FOREIGN PATENT DOCUMENTS

| | | |
|---|---|---|
| JP | 2005223629 A | 8/2005 |
| JP | 2007-026172 A | 2/2007 |
| WO | 2000042533 A1 | 7/2000 |
| WO | 2009/049277 A1 | 4/2009 |
| WO | 2013/093692 A2 | 6/2013 |

\* cited by examiner

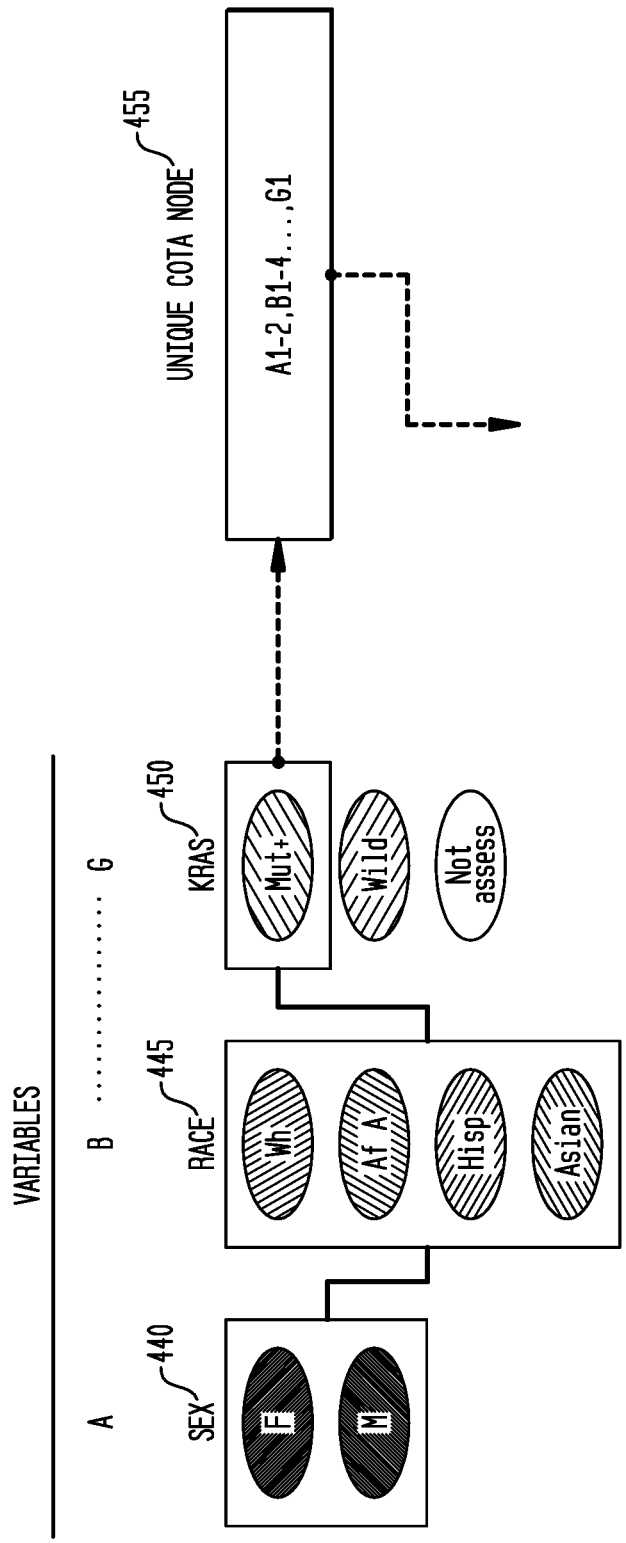

FIG. 10

COTA

Graph Search:
Report For:
- ⦿ Minimal Diagnosis
- ○ Complete Diagnosis
- ☐ Audited Patient

* Diagnosis Type: Lymphoma
Cancer Site/Subtype: Hodgkin's Lymphoma
ICD9 Code: All
Co-Morbidity: --All--
Disease Progression: All
Gender: ○ Male ○ Female ⦿ Both
Age: All
From: 2010
To: 2013
Race: All
Diabetes: --All--

Diagnosis Details Report

View Report

Patient Search tings | Log Out

Analysis

Download PDF — 1005

* Independent Variable:
--Select--
ICD9 Code
Co-Morbidity
Disease Progression
Gender
Age
Race
Diabetes
Tobacco History
Chemo/Radiation History
Stage
Histology
IPI Score
FLIPI Score
MIPI Score
Subtype
IPSS Risk
RISK
Ki-67
HIV
Beta 2 Microglobulin
ZAP 70
IgVH Mutation
p53 Deletion
ALK
BCR-ABL
TCL1
Bulky
Small Cell Variant
B Cell
CD30 Positive
Double Hit 14, 18 with C-MYC translocation
C-MYC
EBV
Anaplastic (CD30+)
B-Symptoms present
Grade
B Symptoms
Hasenclever Prognostic Score
Sub Type (value Diff)
t(4; 11)
CNS involvement at diagnosis
Primary extranasal location
Sub Type Aggressive NK Leukemia All clinical and molecular variables pertinent for lymphoma

COTA | CANCER OUTCOME TRACKING & ANALYSIS — Treatment

Hospital A ▽    Welcome, Jon Smith | Settings | Log Out

Patient | Search | Diagnosis | Outcomes | Treatment | ECOG | Reports | Analysis

Patient Details:
MRN: 999999999   Patient Name: DOE, JANE   Physician: DOE, JOHN   Initial Visit Date: 01-01-2015

Diagnoses Details:
Cancer Site/subtype: Breast Cancer   ICD9 Code: 174.9 Breast (Female), Unspecified (Malignant neoplasm of female breast)   Primary: 1

| Progression 0 | Progression 1 | Progression 2 |

Track 0

Observation: No
Treatment Intent: Curative

Patient Declined:

| Main | Surgery | Anti-Neoplastic Drugs | Anti-Neoplastic Drug Therapy | Cellular Therapy | Radiation Therapy | Toxicity | ALL |

Anti-Neoplastic Category: 4-Neo adjuvant (primary not completely resected-residual disease)   Treatment Intent: Curative ▽

Anti-Neoplastic Category: 4-Neo adjuvant (primary not completely resected-residual disease) ▽

Reason for delivering less than 80% Dose Intensity: --Select-- ▽

☐ Patient Declined Further Surgery
☐ Patient Declined Further Anti-Neoplastic Drug Therapy
☐ Patient Declined cellular Therapy
☐ Patient Declined Further Radiation Therapy

[ Save ] [ Exit ] [ Delete ]

FIG. 15B

COTA | CANCER OUTCOME TRACKING & ANALYSIS    Treatment                    Hospital A  ▽          Welcome, Jon Smith | Settings | Log Out
                                                                    Patient  Search  Diagnosis  Outcomes  [Treatment]  ECOG  Reports  Analysis    ⤴1510

Patient Details:
MRN: 99999999    Patient Name: DOE, JANE                    Physician: DOE, JOHN              Initial Visit Date: 01-01-2015

Diagnosis Detail:
Cancer Site/subtype: Breast Cancer        ICD9 Code: 174.9 Breast (Female), Unspecified (Malignant neoplasm    Primary: 1
                                          of female breast)

| Progression 0 | Progression 1 | Progression 2 |

Track 0
Observation: No                                                                                                                    ⤴1515
Treatment Intent: Curative                 Patient Declined:
                                           Anti-Neoplastic Category: 4-Neo adjuvant (primary not completely resected-residual disease)

| Main | Surgery | Anti-Neoplastic Drugs | Cellular Therapy | Radiation Therapy | Toxicity |

Regimen Start: 31-1-2015 ✕ 🗓   Description: Doxorubicin, Cyclophosphamide
Regimen End:
Dose Intensity:                 Regimen:         ⦿ Diagnosis  ○ All        AC 140 x4            ◆
ECOG PS <3:                     Support Drug(s): ⦿ Generic    ○ Brand      --Select--           ◆

Save     Exit     Delete

Legend:  ✎:Edit  ☑:Close  ☰:Components    ⤴1505

Records per Page: 25 ▽   No. of Records: 2                  Regimen                                                              ⤴1520

| Regimen | Description | Start Date | End Date | 1 | 2 | 3 | 4 | ECOG PS < 3 | Dose Intensity | Action |
|---|---|---|---|---|---|---|---|---|---|---|
| Observation | Observation | 1-1-2015 | 2-6-2015 | 0 | 1 | 0 | 0 | | 100 | ✎☑☰ |
| 5-FU225 CI w/RT x7 weeks | Fluorouracil | 11-1-2015 | 11-15-2015 | 0 | 1 | 0 | 0 | | 55 | ✎☑☰ |

FIG. 16

CO⌒A | CANCER OUTCOME TRACKING & ANALYSIS

Outcomes

Hospital A ▽

Welcome, Jon Smith | Settings | Log Out

Patient Search | Diagnosis | Outcomes | Treatment | ECOG | Reports | Analysis

Search:
* MRN: 999999999          [Search]   [Clear]

Patient Details:
Patient Name: DOE, JANE          Physician: DOE, JOHN          Initial Visit Date: 01-01-2015

Diagnosis Detail:
Cancer Site/subtype: Breast Cancer     ICD9 Code: 174.9 Breast (Female), Unspecified (Malignant neoplasm of female breast)     Primary: 1

| Progression 0 | Progression 1 | Progression 2 |

Track 0
Pathologic Diagnosis: 01-01-2012
Treatment Start: 01-01-2012
Treatment End: 06-01-2012
Response(s) Date: Stable ▽   Stable: 03-01-2012   Partial:              CR-RA-Pet-Negative: CR
Track End Date: Progression ▽   Progression: 06-01-2012   Last Contact:        Death:

Created By: John Doe at 7/8/2015 3:57:57 PM EST
Audited By: John Doe at 8/11/2015 3:45:07 AM EST
Last Modified By: John Doe at 8/11/2015 3:46:16 AM EST

[Save]   [Exit]   [Delete]

☐ Import Lock

1600

DECISION SUPPORT

FIG. 21

COTA — Diagnosis

Welcome, Jon Smith | Settings | Log Out

Patient | Search | Diagnosis | Outcomes | Treatment | Reports | Analysis

Hospital A ▾

Diagnosis Type: [Gastrointestinal Oncology ▾]

* MRN: [999999999]    [Search]

Search: [_____]    [Clear]

Patient Name: [_____]
Physician: [_____]

Patient Details:

Initial Visit Date: ☐
Date of Pathologic Diagnosis: ☐

* Cancer Site/Subtype: [Colon Cancer ▾]
ICD9 Code: [--Select-- ▾]
Co-Morbidity: [0 Vital Organ Dysfunction ▾]
Stage: [--Select-- ▾]
Histology: [--Select-- ▾]
Histologic Grade: [--Select-- ▾]
K-RAS Mutation (Colon): [--Select-- ▾]
CEA at Diagnosis: [--Select-- ▾]
Perineural/Lymphovascular invasion: [Not assessed ▾]
Detected in colorectal cancer (DCC): [Not assessed ▾]
18q loss of heterozygosty (LOH): [Not assessed ▾]
p27 kip1: [--Select-- ▾]
MSI: [--Select-- ▾]
MMR: [--Select-- ▾]
Oncotype DX: [--Select-- ▾]
Residual Tumor: [--Select-- ▾]
BRAF Mutation (Colon): [Not assessed ▾]
NRAS (Colon): [Not assessed ▾]
Disease Progression:
Test Result(s) Pending: ☐

FIG. 22

COTA | Hospital A | Welcome, Jon Smith | Settings | Log Out

Diagnosis | Patient | Search | Diagnosis | Outcomes | Treatment | Reports | Analysis Diagnosis Type: [Breast Oncology]

*MRN: [999999999] [Search]

Patient Name: [          ]    Search: [          ]    Initial Visit Date: [   ]  ☐
Physician: [          ]    [Clear]    Date of Pathologic Diagnosis: [   ]  ☐

── Patient Details: ──

* Cancer Site/Subtype: [Breast Cancer ▼]
ICD9 Code: [--Select-- ▼]
Co-Morbidity: [0 Vital Organ Dysfunction ▼]
Stage: [--Select-- ▼]
Histology: [--Select-- ▼]
Tumor Size: [--Select-- ▼]
Tumor Grade: [--Select-- ▼]
Nodal Involvement: [--Select-- ▼]
Estrogen Receptor: [--Select-- ▼]
Progesterone Receptor: [--Select-- ▼]
Menopausal Status: [--Select-- ▼]
Her2neu: [--Select-- ▼]
Ki67: [Not assessed ▼]
P53: [Not assessed ▼]
Oncotype DX: [--Select-- ▼]
Circulating Tumor Cells/Micro Mets: [Not assessed ▼]
Lymphovascular Invasion: [--Select-- ▼]
BRCA: [--Select-- ▼]
BRCA1: [--Select-- ▼]
BRCA2: [--Select-- ▼]
BART: [--Select-- ▼]
Disease Progression:
Test Result(s) Pending:

FIG. 23

COTA 📊 Diagnosis     Hospital A ▼     Welcome, Jon Smith | Settings | Log Out

Patient   Search   Diagnosis   Outcomes   Treatment   Reports   Analysis

Diagnosis Type: [Thoracic Oncology ▼]

─── Search: ───

*MRN: [____]

Patient Name: [_____]   [ Search ]

Physician: [_____]   [ Clear ]

─── Patient Details: ───

Initial Visit Date: [____] ☐

* Cancer Site/ Subtype: [Lung cancer ▼]                Date of Pathologic Diagnosis: [____] ☐

ICD9 Code: [--Select-- ▼]

Co-Morbidity: [0 Vital Organ Dyfunction ▼]

Stage: [--Select-- ▼]

Histology: [--Select-- ▼]

Histologic Grade: [--Select-- ▼]

EGFR: [--Select-- ▼]

ALK Fusion: [--Select-- ▼]

Pancoast Tumor: [--Select-- ▼]

Disease

Progression:

Test Result(s) Pending: ☐

Last Modified By

[ Save ]    [ Exit ]

CLINICAL OUTCOME TRACKING AND ANALYSIS

CROSS-REFERENCE TO RELATED APPLICATIONS

This application is a continuation of U.S. application Ser. No. 14/507,640 filed on Oct. 6, 2014, which claims the benefit of priority to U.S. provisional application No. 61/888,418 (filed Oct. 8, 2013), the entire contents of which are incorporated by reference herein.

FIELD

The present disclosure relates to the treatment of patients having a disease, and more specifically to clinical outcome tracking and analysis.

BACKGROUND

As the general population is living longer, medical costs associated with the aging population are increasing. The costs associated with diseases, such as cancer, are typically enormous. For example, cancer costs are projected to be the highest growth area in healthcare spending without a commensurate improvement in outcomes. Approximately $125 billion was spent in 2010 on cancer care in the United States alone, and estimates are that approximately 15-30% of the spending can be categorized as "waste". Conventional techniques to control costs, such as clinical pathways and disease management, are typically ineffective, but there are no quality alternatives that currently exist in the market today.

SUMMARY

As advancements in technology and medicine continue to occur, the science and clinical practice of caring for diseases (such as cancer) are rapidly evolving. Often, medical professionals (e.g., oncologists) have a difficult time keeping up with these advancements. These advancements, such as next generation genetic sequencing, are typically complex and may present major issues for health plans and medical professionals. As a result, health plans will likely need more tools and support to manage their medical (e.g., oncology) business. Similarly, medical professionals (e.g., physicians) will need more decision support tools to practice best medicine and stay in business.

As described herein, a clinical outcome tracking and analysis (COTA) module is a tool to, for example, enable medical professionals and/or other users to practice better medicine, better manage and locate specific information associated with a disease and/or patient, and to facilitate improved control of cost.

According to one aspect, the described invention provides a method for clinical outcome tracking and analysis, comprising: receiving one or more parameters; sorting a plurality of patient medical records to provide a sorted set of patient medical records satisfying the one or more parameters; applying a nodal address, indicating one or more variables, to the sorted set of patient medical records to determine a clinically relevant set of patient medical records as the sorted set of patient medical records satisfying the one or more variables; analyzing the clinically relevant set of patient medical records; and transmitting a communication based on the analyzing, wherein the transmitting is to a user to effect treatment, to monitor performance, or to reduce at least one of treatment variability, waste or inefficiency while delivering on intended clinical outcome.

According to one embodiment, the clinical outcome tracking and analysis comprises sorting, outcome tracking, quality of life metrics, toxicity to therapy and cost of care.

According to one embodiment, the parameters for sorting comprise sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care.

According to one embodiment, the nodal address is represented as a plurality of strings of digits, each of the plurality of strings of digits representing one of the one or more variables. According to another embodiment, the one or more variables include the disease-specific clinical molecular phenotype and a string of digits representing the phenotype is determined based on a directed graph. According to another embodiment, the nodal address is associated with one or more bundles of predetermined patient care services for treatment of the disease.

According to one embodiment, analyzing comprises: tracking clinical outcomes of one or more patients associated with a disease; and updating records of the one or more patients with the clinical outcomes of the one or more patients. According to another embodiment, the clinical outcomes comprise at least one of survival, response metrics, quality of life metrics, incidence of drug toxicity, severity of drug toxicity, delivered dose intensity, drugs received, drug interval, drug duration, cost of care, and death. According to another embodiment, analyzing comprises: comparing tracked clinical outcomes between patients in the set of patient medical records. According to another embodiment, analyzing comprises: identifying a specific patient as a candidate for a specific drug. According to another embodiment, analyzing comprises: comparing clinical outcomes between patients based on treatment, cost, or a combination thereof in the set of patient medical records. According to another embodiment, analyzing comprises: comparing a therapy to a quality of life. According to another embodiment, analyzing comprises: comparing outcome performance of a medical professional treating a disease to outcome performance of an aggregate of medical professionals treating the disease.

According to one embodiment, transmitting a communication comprises: sending at least a portion of the analyzed set of patient medical records to a client device for display. According to another embodiment, transmitting a communication comprises: transmitting, in response to a trigger, an alert to a client device, the trigger comprising at least one of diagnosis, progression, dose change, drug change, toxicity, trending towards variance from a desired outcome, and a specific time.

According to one embodiment, the method minimizes biological variability of clinical outcome.

According to another aspect, the described invention provides an apparatus for clinical outcome tracking and analysis comprising: a processor; and a memory to store computer program instructions, the computer program instructions when executed on the processor cause the processor to perform operations comprising: receiving one or more parameters; sorting a plurality of patient medical records to provide a set of patient medical records satisfying the one or more parameters; applying a nodal address, indicating one or more variables, to the sorted set of patient medical records to determine a clinically relevant set of patient medical records as the sorted set of patient medical records satisfying the one or more variables; analyzing the clinically relevant set of patient medical records; and transmitting a communication based on the analyzing, wherein the transmitting is to a user to effect treatment, to monitor performance, or to reduce at least one of treatment variability, waste or inefficiency while delivering on intended outcome.

According to one embodiment, the clinical outcome tracking and analysis comprises sorting, outcome tracking, quality of life metrics, toxicity to therapy and cost of care.

According to one embodiment, the parameters for sorting comprise sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers and cost of care.

According to one embodiment, the nodal address is represented as a plurality of strings of digits, each of the plurality of strings of digits representing one of the one or more variables. According to another embodiment, the one or more variables include the disease-specific clinical molecular phenotype and a string of digits representing the phenotype is determined based on a directed graph. According to another embodiment, the nodal address is associated with one or more bundles of predetermined patient care services for treatment of the disease.

According to another aspect, the described invention provides a computer readable medium storing computer program instructions for clinical outcome tracking and analysis which, when executed on a processor, cause the processor to perform operations comprising: receiving one or more parameters; sorting a plurality of patient medical records to provide a set of patient medical records satisfying the one or more parameters; applying a nodal address, indicating one or more variables, to the sorted set of patient medical records to determine a clinically relevant set of patient medical records as the sorted set of patient medical records satisfying the one or more variables; analyzing the clinically relevant set of patient medical records; and transmitting a communication based on the analyzing, wherein the transmitting is to a user to effect treatment, to monitor performance, or to reduce at least one of treatment variability, waste or inefficiency while delivering on intended outcome.

According to one embodiment, the clinical outcome tracking and analysis comprises sorting, outcome tracking, quality of life metrics, toxicity to therapy and cost of care.

According to one embodiment, the parameters comprise sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers and cost of care.

According to one embodiment, analyzing comprises one or more of: (a) tracking clinical outcomes of one or more patients associated with a disease and updating records of the one or more patients with the clinical outcomes; (b) comparing clinical outcomes between patients based on treatment, cost, or a combination thereof in the set of patient medical records; (c) comparing tracked clinical outcomes between patients in the set of patient medical records; (d) identifying a specific patient as a candidate for a specific drug; (e) comparing clinical outcome between patients based on treatment, cost, or a combination thereof in the set of patient medical records; (f) comparing a therapy to a quality of life.

According to one embodiment, the clinical outcomes comprise at least one of survival, response metrics, quality of life metrics, incidence of drug toxicity, severity of drug toxicity, delivered dose intensity, drugs received, drug interval, drug duration, cost of care, and death.

According to one embodiment, transmitting a communication comprises: sending at least a portion of the analyzed set of patient medical records to a client device for display. According to another embodiment, transmitting a communication comprises: transmitting, in response to a trigger, an alert to a client device, the trigger comprising at least one of diagnosis, progression, dose change, drug change, toxicity, trending towards variance from a desired outcome, and a specific time.

These and other aspects and embodiments will be apparent to those of ordinary skill in the art by reference to the following detailed description and the accompanying drawings.

BRIEF DESCRIPTION OF THE DRAWINGS

In the drawing figures, which are not to scale, and where like reference numerals indicate like elements throughout the several views:

FIG. 4B is a flow diagram of the COTA module sorting data through specific node creation in accordance with an embodiment of the present disclosure;

FIG. 10 shows a listing of a plurality of variables pertinent to a particular disease in accordance with an embodiment of the present disclosure;

FIGS. 15A and 15B are graphical representations of a treatment interface in accordance with an embodiment of the present disclosure;

FIG. 16. is a graphical representation of an outcome screen in accordance with an embodiment of the present disclosure;

FIGS. 21-23 display embodiments of graphical representations for different diagnosis types in accordance with an embodiment of the present disclosure;

DESCRIPTION OF EMBODIMENTS

Figure 1:
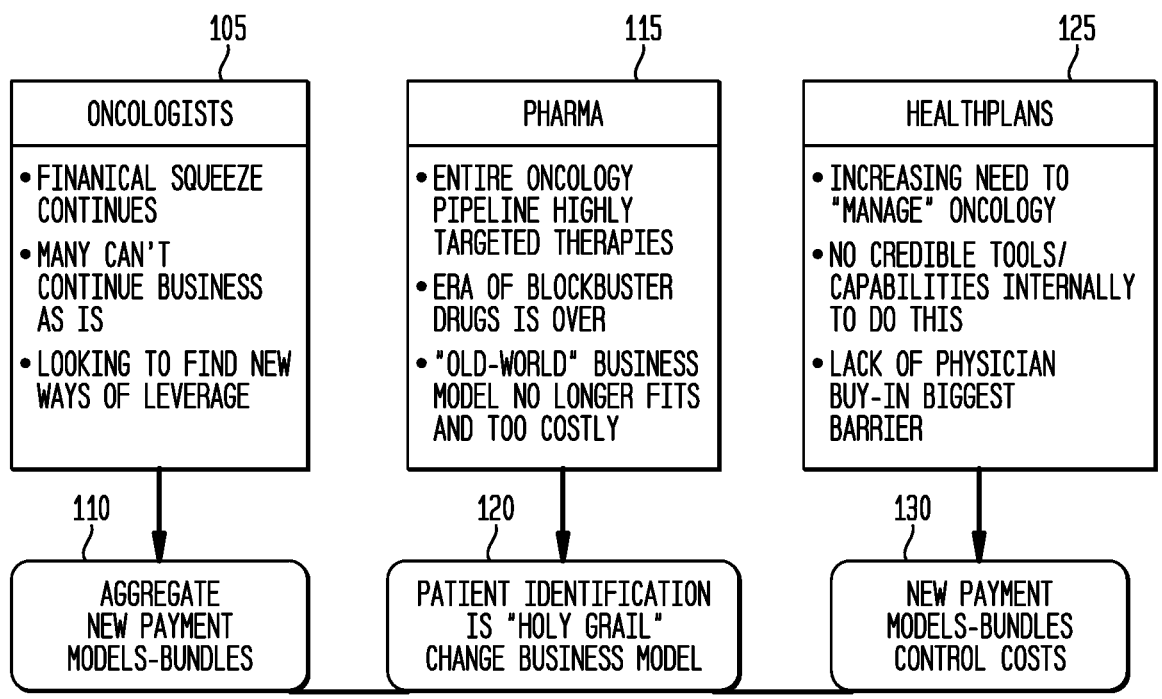
FIG. 1 illustrates a block diagram of an example of some of the pressures in the oncology market and some potential solutions.

Embodiments are now discussed in more detail referring to the drawings that accompany the present application. In the accompanying drawings, like and/or corresponding elements are referred to by like reference numbers.

Various embodiments are disclosed herein; however, it is to be understood that the disclosed embodiments and user interfaces as shown are merely illustrative of the disclosure that can be embodied in various forms. In addition, each of the examples given in connection with the various embodiments is intended to be illustrative, and not restrictive. Further, the figures are not necessarily to scale, some features may be exaggerated to show details of particular components (and any size, material and similar details shown in the figures are intended to be illustrative and not restrictive). Therefore, specific structural and functional details disclosed herein are not to be interpreted as limiting, but merely as a representative basis for teaching one skilled in the art to variously employ the disclosed embodiments.

The present invention is described below with reference to block diagrams and operational illustrations of methods and devices to select and present media related to a specific topic. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved. Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Although described with respect to cancer conditions, the described clinical outcome therapeutic analysis can be used for any clinical condition (e.g., cardiovascular disease, metabolic disease (diabetes), immune mediated diseases (e.g., lupus, rheumatoid arthritis), organ transplantation; neurodegenerative disorders; pulmonary diseases, infectious diseases, hepatic disorders). A practitioner would know the parameters of each such condition.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The pharmaceutical industry has placed most of its research and development (R&D) investments into specialty compounds with oncology as the lead category. For example, approximately 30-35% of Phase 3 pipeline is oncology. These compounds are highly targeted, specialized therapies based on latest scientific advances and will likely require a commercial and development model different from the one that exists today. Pharmaceutical companies' current structures are typically inefficient and likely cannot be supported by their future products.

Diagnostic companies developing new companion diagnostic tests for new generation therapies will need new ways to educate physicians and efficient sales and distribution channels.

The reimbursement model in the U.S. will likely change from a fee-for-service model to a value-based payment model. The Affordable Care Act has accelerated certain elements of this (e.g., accountable care organizations (ACOs) & patient centered medical home (PCMHs) models for primary care) and there is payer activity towards bundling payments within specialties (e.g. orthopedics). The current fee-for-service payment model is likely not sustainable for the government, employers, other payers, and/or for physicians. Many oncologists are also finding the economics of a fee-for-service model unsustainable. As indicated above, the government is likely moving towards value-based payment models.

FIG. 1 illustrates a block diagram of an example of some of the pressures in, for example, the oncology market and some potential solutions. Oncologists 105 face financial pressures, many cannot continue business with their current models, and many are looking to find new ways of leverage. Potential oncologist solutions 110 include aggregating and new payment models, such as bundles. Pharmaceutical companies (shown as "Pharma") 115 typically have much or all of their oncology pipeline as highly targeted therapies. Additionally, the era of blockbuster drugs is likely over. Further, the "old-world" business model may no longer fit and may be too costly. Possible pharmaceutical solutions 120 include patient identification and changing their business model. Health plans 125 typically have an increasing need to "manage" oncology. Also, there are no credible tools or capabilities internally to perform this management. Additionally, medical professionals such as physicians may not buy into the health plans. Potential health plan solutions 130 include new payment models (e.g., bundles) and controlling costs.

Figure 2:
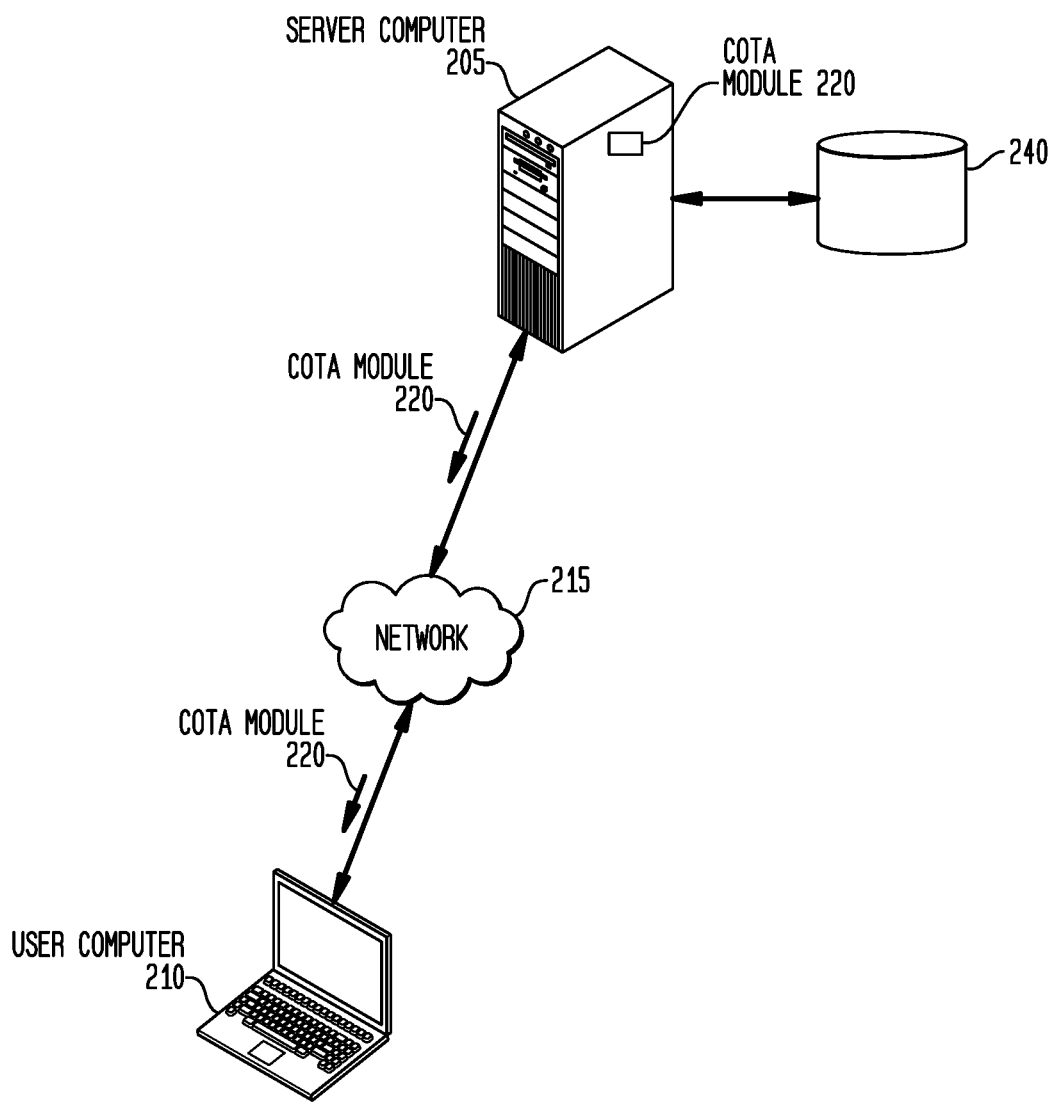
FIG. 2 illustrates a block diagram of a server computer communicating with a user computer over a network to provide a clinical outcome tracking and analysis (COTA) module to the user computer in accordance with an embodiment of the present disclosure.

FIG. 2 illustrates a block diagram of a server computer 205 (also referred to below as server 205) communicating with a user computer (also referred to herein as client device) 210 over network 215 to provide a clinical outcome tracking and analysis (COTA) module 220 to the user computer 210 in accordance with one embodiment. Server 205 may generate and/or serve web pages, for example, to be displayed by a browser (not shown) of user computer 210 over network 215 such as the Internet. In one embodiment, the COTA module 220 is a web page (or is part of a web page) and is therefore accessed by a user of the user computer 210 via a web browser. In another embodiment, the COTA module 220 is a software application, such as a mobile "app", that can be downloaded to the user computer 210 from the server computer 205. In a further embodiment the COTA module 220 provides a user interface for enabling the functionality described herein.

A computing device such as server computer 205 and user computer 210 may be capable of sending or receiving signals, such as via a wired or wireless network, or may be capable of processing or storing signals, such as in memory as physical memory states. Devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows® Server, Mac® OS X®, Unix®, Linux®, FreeBSD®, or the like.

Server 205 may include a device that includes a configuration to provide content via a network to another device. Server 205 may, for example, host a site, such as a social networking site, examples of which may include, without limitation, Flickr®, Twitter®, Facebook®, LinkedIn®, or a personal user site (such as a blog, vlog, etc.). Server 205 may also host a variety of other sites, including, but not limited to, business sites, educational sites, dictionary sites, encyclopedia sites, wikis, financial sites, government sites, etc.

Server 205 may further provide a variety of services that include, but are not limited to, web services, third-party services, audio services, video services, email services, instant messaging (IM) services, SMS services, MMS services, FTP services, voice over IP (VOIP) services, calendaring services, photo services, or the like. Examples of content may include text, images, audio, video, or the like, which may be processed in the form of physical signals, such as electrical signals, for example, or may be stored in memory, as physical states, for example. Examples of devices that may operate as a server include desktop computers, multiprocessor systems, microprocessor-type or programmable consumer electronics, etc.

In one embodiment, the server 205 hosts or is in communication with a database 240. The database 240 may be stored locally or remotely from the server 205. In one embodiment, the COTA module 220 accesses or searches or sorts the data stored in database 240. The COTA module 220 may also retrieve information over network 215 (e.g., from the Internet). Database 240 may store patient data or other pertinent medical information. For example, the data entered into the database or the COTA module 220 may be from experts in their respective fields (e.g., oncologists with more than 5, 10, 15, 20, 30, etc. years of experience). The data can be entered into the database 240 and/or the COTA module 220 manually or automatically.

A network may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, or any combination thereof. Likewise, sub-networks, such as may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a telephone line or link, for example.

A wireless network may couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly. A wireless network may further employ a plurality of network access technologies, including Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

In one embodiment and as described herein, the user computer 210 is a smartphone. In another embodiment, the user computer 210 is a tablet. The user computer 210 can also be a computer, a music player, a set-top box, a smart TV, or any other computing device.

The COTA module 220 can establish an effective way to manage patients, resulting in better outcomes at controlled costs. In one embodiment, the COTA module 220 is the connector or interface between third parties and medical professionals (e.g., oncologists). In one embodiment, the COTA module 220 is an analytic tool that sorts cancers to the highest level of clinical and molecular fidelity. The COTA module 220 then tracks outcomes in real-time, such as overall survival (OS), Progression free survival (PFS), and cost.

Overall survival may be a trial endpoint, which is usually expressed as a period of time (survival duration), e.g., in months. Frequently, the median is used so that the trial endpoint can be calculated once 50% of subjects have reached the endpoint. An example is disease free survival, which is usually used to analyze the results of the treatment for the localized disease which renders the patient apparently disease free, such as surgery or surgery plus adjuvant therapy. In the disease-free survival, the event is relapse rather than death. The people who relapse are still surviving but they are no longer considered disease-free.

Progression free survival is the length of time during and after medication or treatment during which the disease being treated (e.g., cancer) does not get worse. It is sometimes used as a metric to study the health of a person with a disease to try to determine how well a new treatment is working.

As used herein, the term "real-time" or "real time" means without perceivable delay or information that is delivered immediately after collection or processing. These terms also include a time delay introduced by automated processing (e.g., near real-time).

In one embodiment, the COTA module 220 can alert the user of the user computer 210 (e.g., medical professional) at key moments to provide relevant information. The COTA module 220 can also enable communication and collaboration between medical professionals as well as content publishing (e.g., by medical professionals). In one embodiment, COTA module 220 can enable medical professionals to execute at-risk contracts (e.g., bundled payments) with payers.

Although the COTA module 220 is described herein with respect to cancer, the COTA module 220 can be utilized advantageously to manage any disease or condition.

In one embodiment, descriptive elements of COTA include sorting, outcome tracking, performance status/quality of life metrics, toxicity to therapy and cost of care.

Figure 3:
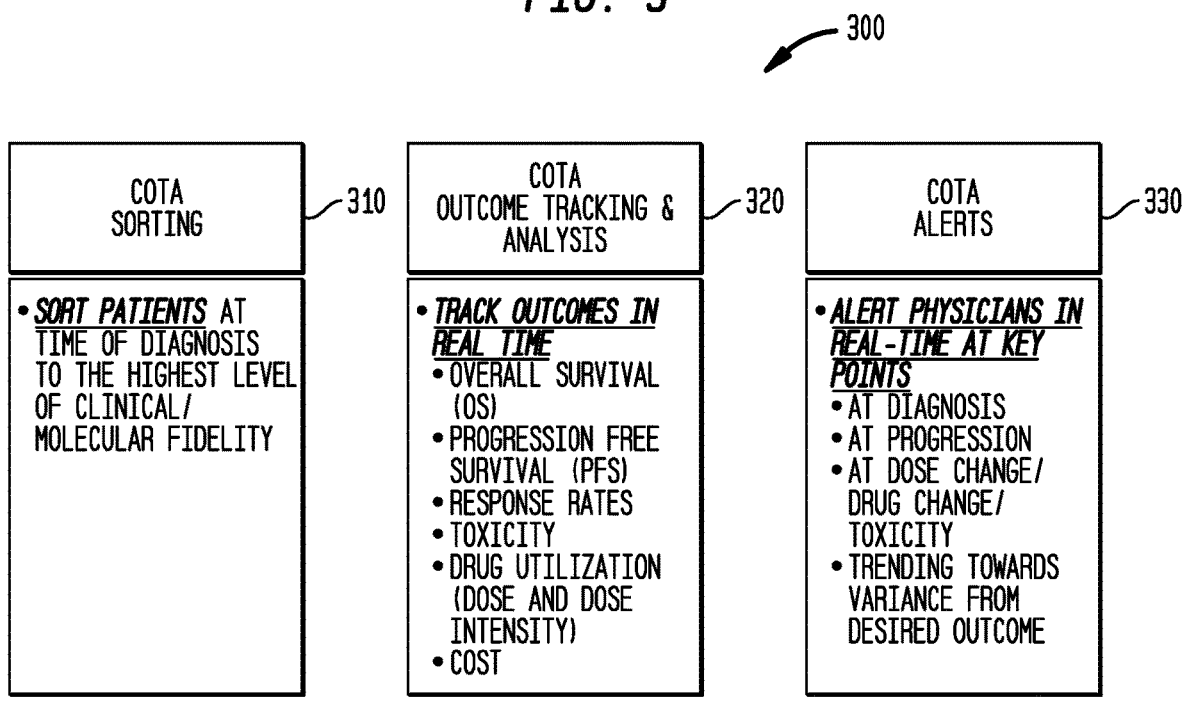
FIG. 3 is a block diagram illustrating several functions provided by the COTA module in accordance with an embodiment of the present disclosure.

FIG. 3 is a block diagram illustrating functions 300 provided by the COTA module 220 in accordance with one embodiment.

In one embodiment, the COTA module 220 performs COTA sorting 310, which identifies patients satisfying one or more parameters. Parameters may include, for example, demographic parameters, e.g., sex, age, ethnicity, comorbidities, tobacco use, medical record number, source of insurance, primary care medical professional, referring medical professional, hospital, approved service vendors (e.g., pharmacy), disease specific clinical and molecular phenotype, therapy intent, stage of therapy with respect to progression of disease, and biomarkers. The parameters may be a simple indicator (e.g., positive, negative, not accessed), a numerically based parameter (e.g., tumor size), a standards based parameter (e.g., tumor grade), etc. The parameters may be received by the COTA module 220 as a user selected input. Patients may be sorted 310 at the time of diagnosis to the highest level of clinical and/or molecular fidelity because each patient has different mortality, morbidity, treatments and costs. The term "highest level of clinical and/or molecular fidelity" refers to the highest level of patient information available according to the latest scientific and/or medical guidelines as accepted in its pertinent field. For example, where there are, e.g., 10 tests available for lung cancer, results of the 10 tests represent the highest level of fidelity for lung cancer. The COTA module 220 may sort patients with lung cancer with any combination of those 10 results. The COTA module 220 may include additional scientific and/or medical guidelines as they become accepted in its pertinent field. In one embodiment the COTA module 220 collects all information that impacts survival and/or prognosis and/or treatment of a patient based on the latest scientific and/or medical guidelines.

Further, the COTA module 220 performs outcome tracking and analysis 320. The COTA module 220 tracks outcomes in real time. In one embodiment, the element Outcome Tracking includes the parameters progression free survival, overall survival, performance status/quality of life metrics, incidence/severity of toxicity, (e.g., the degree to which a substance or drug can damage an individual), death, and drug utilization (e.g., delivered dose intensity, dose interval and duration of therapy) Other types of outcomes are also contemplated.

The element ECOG performance status/quality of life metrics refers to a method by which the quality of life of the patient over time can be tracked. It is part of the demographic parameter disease specific clinical molecular phenotype, i.e., the stage of a patient's health at the start of therapy, and is within Sorting. For example, a comparison of ECOG at start of therapy (e.g., ECOG of 3), with ECOG after therapy (e.g., ECOG of 2) reflects the effect of the therapy.

In one embodiment, exemplary parameters of the element Toxicity to Therapy are incidence and severity. In one embodiment, COTA enables at risk financial contracting between payers and providers so the parties can reduce variability, waste and inefficiency but yet deliver on the intended outcome.

The COTA module 220 can also transmit communications, such as alerts 330, to medical professionals (e.g., physicians) (or, in another embodiment, to a patient's insurance company or any other entity) in real-time at key points, such as, e.g., at diagnosis, at progression, at dose change/drug change/toxicity, and/or trending towards variance from desired outcome. In one embodiment, the COTA module 220 provides alerts to medical professionals that identify a specific patient for which the medical professional is searching. For example, the COTA module 220 may provide an alert in real time to a pharmaceutical company that is looking for specific patients to administer a specific (e.g., new) drug or drug candidate. The alert may identify a specific patient that is a good candidate for the specific drug.

Figure 4A:
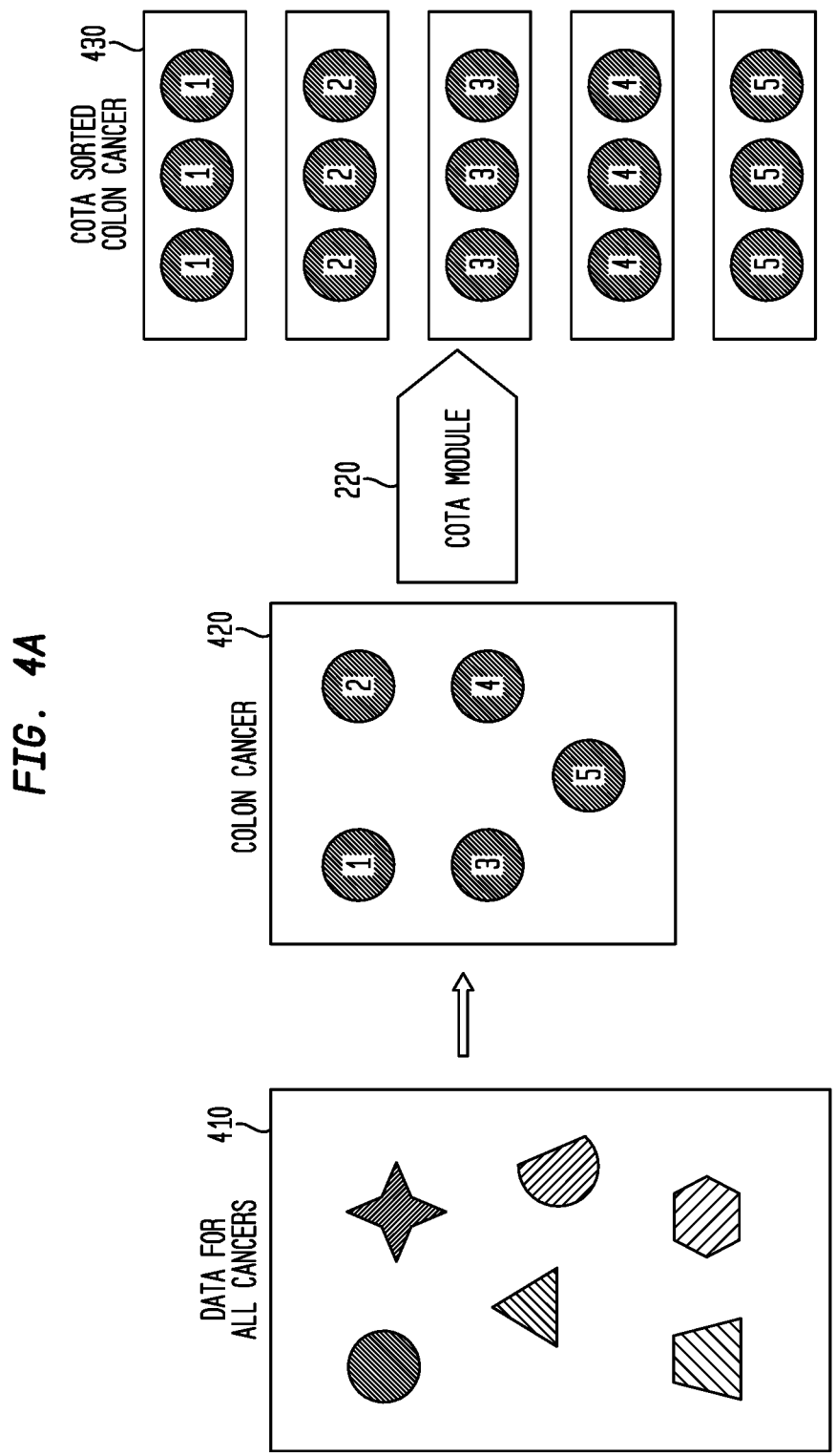
FIG. 4A is a block diagram illustrating use of the COTA module to sort data associated with colon cancer patients in accordance with an embodiment of the present disclosure.

FIG. 4A is a block diagram illustrating sorting data associated with colon cancer patients in accordance with one embodiment. Although described with respect to cancer, e.g., colon cancer, the description and figure can apply to any type of cancer or, in another embodiment, any type of disease for which there is data associated with patients.

Data 410 is gathered for all cancers (or, in another embodiment, for more than one type of cancer, or, in other embodiments, for all cardiovascular diseases, pulmonary diseases, gastrointestinal diseases, neurological diseases, etc), and this data 410 is narrowed to a subset 420 relating to, e.g., colon cancer. In one embodiment, the subset 420 of data relating to colon cancer is then analyzed and sorted by the COTA module 220 to produce a sorted colon cancer data set 430. The sorted colon cancer data set 430 can include one or more groupings, where each grouping includes data associated with patients having the same type of specific colon cancer. Thus, the COTA module 220 enables the sorting of cancers to the highest level of fidelity.

Typically, patient information is stored in electronic medical records (EMRs). EMRs, however, often contain too much information and it is therefore difficult for a medical professional to locate specific information of interest from the large amount of information stored in EMRs. Further, most of the information in EMRs is not relevant to the information for which the medical professional is searching. Unlike EMRs, whose goal is to capture all or most of the data associated with a patient coming into a doctor's office and the patient leaving the doctor's office, the COTA module 220 is targeted, as the module 220 enables a user to locate specific data associated with particular patients. Accordingly, the COTA module 220 can sort the data to locate specific, specialized information. The data that the COTA module 220 receives is typically via a web page, and is discrete (e.g., typically provided by a user selecting one or more choices in a drop down menu or via one or more check boxes).

COTA classifies, sorts, and facilitates the grouping of types of patients based on these variables results in the designation of a unique COTA nodal address (CNA), which embodies those classification variables. In one embodiment, data is ingested into the system via a human user or a technical process, e.g., an API, a layer (meaning a part of the application which performs a particular function) in the application looks at, and assesses, the information, e.g., whether it is correct, whether it is corrupt, what information is there, what information is missing//holes in the information, how it is formatted, spelling, etc., corrects any problems with the information it detects to date, and assigns a COTA nodal address (CNA) to that set of information. In one embodiment, the CNA is an address to classify like data. In one embodiment, COTA identifies the relationship between different characteristics in a grouping, which allows COTA to classify information on any patient in the grouping. In one embodiment, the set of information sitting in the database is preassigned a CNA. In one embodiment, COTA takes a large amount of information that encompasses many different attributes, allows the user to identify certain of the attributes as a set of characteristics, and adds an attribute(s) to the information to say that the information is similar to other pieces of information in the database, i.e., this information is of the same kind/value as the other information. Accordingly, the nodal address is a number that enables a user to specifically compare like patients to like patients. This specificity allows for minimizing biological variability of outcome and as a consequence provides greater precision regarding the effect of therapeutic agents on outcome.

In one embodiment, a user wants to validate personal health information (PHI) from a patient, make sure it is correct in every way, and then assign the appropriate CNA. As used herein, personal health information (PHI) refers to any information in a medical record or designated record set that can be used to identify an individual patient and that was created, used, or disclosed in the course of providing a health care service such as diagnosis or treatment. Examples of personal identifiers in PHI include, without limitation, name, all geographical subdivisions smaller than a state, including street address, city, county, precinct, zip code; all elements of dates (except year) for dates directly related to an individual, including birth date, admission date, discharge date, date of death, and all ages over 89 and all elements of date (including year) indicative of such age; phone numbers; fax numbers; electronic mail addresses; social security numbers, medical record numbers; health plan beneficiary numbers; account numbers; certificate/license numbers; vehicle identifiers and serial numbers, including license plate numbers; device identifiers and serial numbers; web Universal Resource Locators (URLs); Internet Protocol (IP) address numbers; biometric identifiers, including finger and voice prints; full face photographic images and any comparable images; and any other unique identifying number, characteristic, or code (but not the unique code assigned by the investigator to code the data). This PHI is input for patient A into a browser. The PHI gets sent to a classification layer and a CAN is assigned, the CAN defining attributes of patient A's record. and then into the database, i.e., the set of patient attributes, which falls under this type of CAN, is joined to the CNA. Once this is complete, the next time a user logs into the application and accesses the database, the database will return all of patient A's information and the CNA assigned. Accordingly, the user immediately understands how this patient's symptoms/attributes should be handled, i.e., the user gets a snapshot of how that type of patient relates to other patients whose information is in the database.

FIG. 4B is a flow diagram of COTA classifying and sorting as described above through specific node creation in accordance with one embodiment As shown in FIG. 4B, an expert selects the variables sex or gender 440 (variable A), race 445 (variable B), . . . , and KRAS 450 (variable G). K-Ras is a protein that in humans is encoded by the KRAS gene. The protein product of the normal KRAS gene performs an essential function in normal tissue signaling, and the mutation of a KRAS gene is an important step in the development of many cancers.

The COTA module 220 analyzes the classified and sorted data 430 with respect to these variables (e.g., variables 440, 445, 450) to generate a unique COTA node 455. The COTA module 220 may apply these nodes on the classified and sorted data to provide more clinically relevant results. The nodes are created as a set of preselected variables which are applied to further filter the classified and sorted data. The nodes are represented as nodal addresses indicating the preselected variables. The variables may include, e.g., diagnoses, demographics, outcomes, phenotypes, etc. A phenotype is the composite of a person's observable characteristics or traits, such as its morphology, development, biochemical or physiological properties, phenology, behavior, and products of behavior. Phenotypes result from the expression of a person's genes as well as the influence of environmental factors and the interactions between the two. In one embodiment, the variables of a node are selected by experts in the pertinent field in order to partition the data into clinically relevant results.

The COTA node 455 is represented as a nodal address within the COTA module 220. In one embodiment, the nodal address is represented as a list of the variables selected (as a function of a letter representing the variable and a number representing the selection within the variable). For example, as shown in FIG. 4B, the node 455 includes A1-2 (A represents the sex or gender variable, and 1-2 represents Female and Male patients) shown with a block around both Female and Male variables of Sex variable A. The node 455 also includes B1-4 because the node 455 includes the Race variable with all of the sub-variables selected (shown with a box around all of the Race variables). The node 455 also includes G1, as with respect to the KRAS variable, only Mut+ is selected (boxed). Thus, node 455 has a node address of A1-2, B1-4 . . . , G1.

In another embodiment, the node address is represented as a plurality of strings of digits separated by periods, where each string of digits indicates one or more variables (e.g., disease, phenotype, therapy type, progression/track, sex, etc.). For example, a first string of digits may represent a particular disease, a second string of digits may represent a type of the disease, a third string of digits may indicate a subtype of the disease, and a fourth string of digits may indicate a phenotype. Thus, in this example, the first string of digits may be 01 indicating cancer, the second string of digits may be 02 indicating breast oncology, a third string of digits may be 01 indicating breast cancer, and a fourth string of digits may be 1201 representing particular characteristics of a phenotype such that the nodal address is 01.02.01.1201. It should be understood that the nodal address may include any number of strings of digits and is not limited to four strings.

Figure 4C:
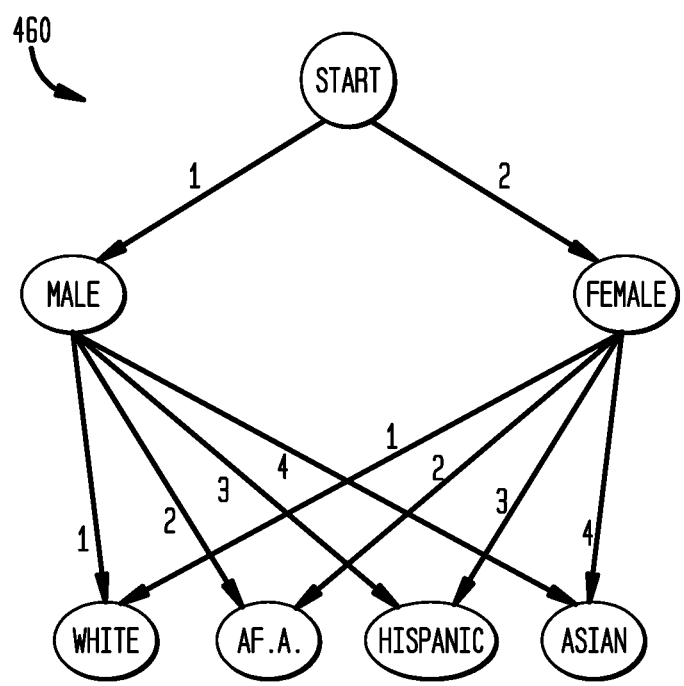
FIG. 4C is a block diagram illustrating a directed graph for determining a string of digits representing phenotype characteristics for nodal addressing in accordance with an embodiment of the present disclosure.

In one embodiment, the string of digits representing the phenotype may be provided by representing characteristics of the phenotype as a directed graph. FIG. 4C illustratively depicts a directed graph 460 showing characteristics of a phenotype to provide a string of digits representing the phenotype in accordance with one embodiment. The directed graph 460 includes nodes representing phenotypes and edges representing a relationship between nodes. The graph is traced starting from root "start" node to nodes for a selected phenotype. Each edge is associated with a number. The string of digits representing the phenotype for the node address is provided as a combination of the numbers. For example, the string of digits for selected phenotype characteristics of male and white would be represented as 11. Other types of combinations may also be employed. Advantageously, representing characteristics of the phenotype as a directed graph allows for the addition of other nodes without changing the entire structure. The screen's appearance is a result of the COTA nodal addresses (CNA), and its appearance can be changed however it is desired to present the information.

Node 455 provides the COTA module 220 with the ability to match resources and alerts specific to each phenotype where relevant. Resources can be information, content, link to live support, etc. Each patient is categorized into one or more nodal addresses. One or more nodes may also be associated with each disease. In one embodiment, resources get "tagged" with appropriate, relevant nodes. In one embodiment, nodes are fungible over time to stay current with scientific/medical advances.

Each nodal address may be associated with one or more bundles of predetermined patient care services (e.g., treatment plans). Each bundle may also be associated with one or more nodes. The services included in each bundle may be determined by one or more medical professionals, a hospital, a group, an insurance company, etc. to optimize patient care and/or cost. In one example, a bundle may indicate a number of imaging scans, a drug or choice of drugs, a schedule of when to administer the drugs, an operation or procedure, a number and frequency of follow up visits, etc. The bundling of patient care services may be particularly useful for risk contracting. For example, each bundle corresponding to a nodal address (associated with a particular disease) may have a predetermined cost allowing a user (e.g., doctor, patient, etc.) to choose an appropriate bundle. The cost may be determined or negotiated based on historical data associated with that particular disease or nodal address. Advantageously, the bundling of services provides cost certainty to an insurance company and/or hospital for a particular disease. This also reduces the cost of processing and maintaining records. Additionally, medical professionals will know ahead of time the predetermined course of treatment, which provides incentives to physicians to obtain better outcomes at lower costs.

Figure 5:
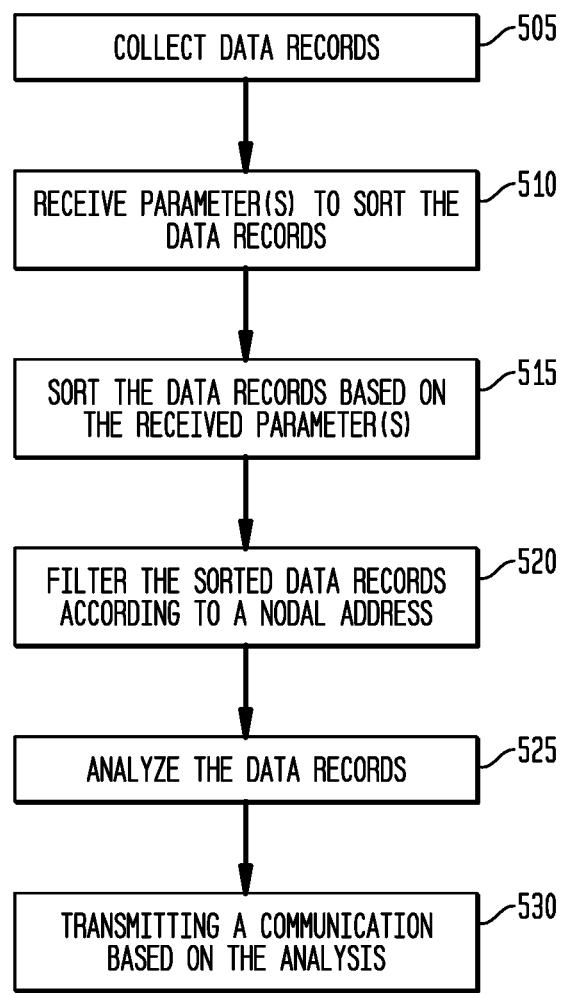
FIG. 5 is a flowchart illustrating steps performed by the COTA module in accordance with an embodiment of the present disclosure.

FIG. 5 is a flowchart illustrating steps performed by the COTA module 220 in accordance with one embodiment. At step 505, the COTA module 220 collects data records. The data records each include data associated with a disease (e.g., cancer). The data records may include patent data for patients who have or who previously had the disease. For example, the data records may include diagnoses, demographics, outcomes, costs, or other pertinent information. The data records may be collected from an electronic database (e.g., an electronic medical record), provided by a user (e.g., medical professional, expert, specialist, etc.), or from any other source. In one embodiment, the COTA module 220 stores the data records in database 240.

At step 510, the COTA module 220 receives one or more parameters to sort the data records. The one or more parameters may be received from the user computer 210 as user selected input. The one or more parameters may include, e.g., diagnoses, demographics, outcomes, costs, or any other parameter.

At step 515, the COTA module 220 sorts the data records based on the one or more parameters. The sorting identifies patients satisfying the one or more parameters. Patients are sorted to the highest level of clinical and/or molecular fidelity based on the latest scientific and/or medial guidelines accept in the pertinent field. In one embodiment, the sorting is performed in real time.

At step 520, the classified and sorted data records are filtered according to a nodal address. The nodal address represents variables preselected by users to provide a set of clinically relevant patients. In one embodiment, the variables of a nodal address are selected by experts in the field. The nodal address may be represented as a plurality of strings of digits each separated by a period. The each string of digits may represent one or more variables (e.g., a disease, type of disease, subtype of disease, phenotypes, or any other relevant variable). Other representations of the nodal address are also contemplated.

At step 525, the data records for the clinically relevant patients are analyzed. Analyzing the data records may include tracking (e.g., in real time) clinical outcomes of patients associated with the disease. The outcomes may include, for example, delivered dose intensity, therapeutic agents received, dose, dose interval, and dose duration, incidence and severity of toxicity, cost, progression free survival (PFS), overall survival (OS), response rates, etc. The COTA module 220 may compare the tracked outcomes between patients. The COTA module 220 may also determine, based on the tracking, whether a specific doctor associated with a tracked patient is treating the patient in accordance with treatment techniques of other doctors treating other (similar) patients. In one embodiment, the COTA module 220 determines this based on the outcomes of many patients.

In another embodiment, analyzing the data records may include updating (e.g., in real time) at least some of the data records based on the tracked outcomes. For example, the COTA module 220 may determine that patient ABC had colon cancer, was prescribed and has taken medication XYZ for two years, and is now in remission for the past 3 years. If the COTA module 220 determines this information from the tracking of patient ABC, the module 220 can update the data record associated with patient ABC with this information.

In other embodiments, analyzing the data records includes performing an analysis to determine patient survival rate, such as, e.g., by creating a Kaplan Meier curve. A Kaplan Meier curve is a curve that shows five year survival rate that can be developed, e.g., for a single doctor (or medical professional) or for a group of doctors (or medical professionals). A Kaplan Meier curve can be created for overall survival and/or progression free survival. Other types of analyses are also contemplated.

To facilitate analyzing, the COTA module 220 may also include an analysis tool to the user computer 210. This analysis tool may be a user interface that is accessible via a web page, a tab on an existing web page, a software application, an app, etc. The user interfaces as depicted in the figures herein are exemplary. This analysis tool may enable a user to compare, analyze, or further sort the data records.

At step 530, the COTA module 220 provides a communication based on the analysis. The communication may be in the form of an alert to a user. In one embodiment, the COTA module 220 may communicate the classified and sorted data records and/or the updated data records to the user computer 210. For example, the COTA module 220 communicates a table, chart, list, link, etc. that enables the user to access the sorted or updated data records. In another embodiment, the COTA module 220 may transmit advertisements with (e.g., related to) the data records to the user computer 210. In other embodiments, the COTA module 220 may identify a specific patient as a candidate for a specific treatment or drug. This information may be valuable to, e.g., a pharmaceutical company, a health plan, a managed care consortium, an insurer, etc. The COTA module 220 may transmit the communication to the user computer 210 or any other entity (e.g., via network 215).

The COTA module 220 can be used by and benefit many people, professionals, and/or companies. For example and as described above, the highly specialized pipeline of pharmaceutical companies likely requires a new business model for many aspects (e.g., development including Phase 4 trials/post-marketing surveillance, marketing, sales, pricing, and contracting). In one embodiment, the professionals at the pharmaceutical companies can use the COTA module 220 to facilitate this new business model. For example, the COTA module 220 can match the right patient to the right drug. The COTA module 220 can enable precise patient identification via its sorting and nodal addressing abilities. In one embodiment, the COTA module 220 provides a matching function that enables a user (e.g., a pharmaceutical company) to locate (e.g., in real time) one or more patients that are or would be good candidates for a specific drug that the pharmaceutical company has released or is developing.

Further, the COTA module 220 may benefit health plans. As indicated above, cancer care will likely become more complex, and it will likely not be efficient for health plans to continue with direct management. In one embodiment, health plans outsource their cancer care to the COTA module 220 (similar to what health plans previously did with pharmacy benefits). This may reduce their costs, such as by reducing total cost of care and providing cost offsets for them, such as by replacing pathways, decreasing expensive prior authorization infrastructure, decreasing other personnel who "manage cancer". Additionally, provisions in the U.S. Affordable Care Act state that 85% of premiums must go to clinical care related activities versus administrative costs. In one embodiment, the COTA module 220 provides an analytic interface with connections to claims data to support health plans in managing their oncologists.

In one embodiment, the COTA module 220 can benefit organizations engaged in diagnostic methods or tools. Organizations engaged in diagnostic methods or tools, such as those involved in next generation genetic sequencing, will likely need an efficient education, marketing and sales/distribution channel. Because the COTA module 220 is able to precisely sort and identify patients and send time based alerts to physicians (or other medical professionals), its use may benefit such organizations.

Figure 6:
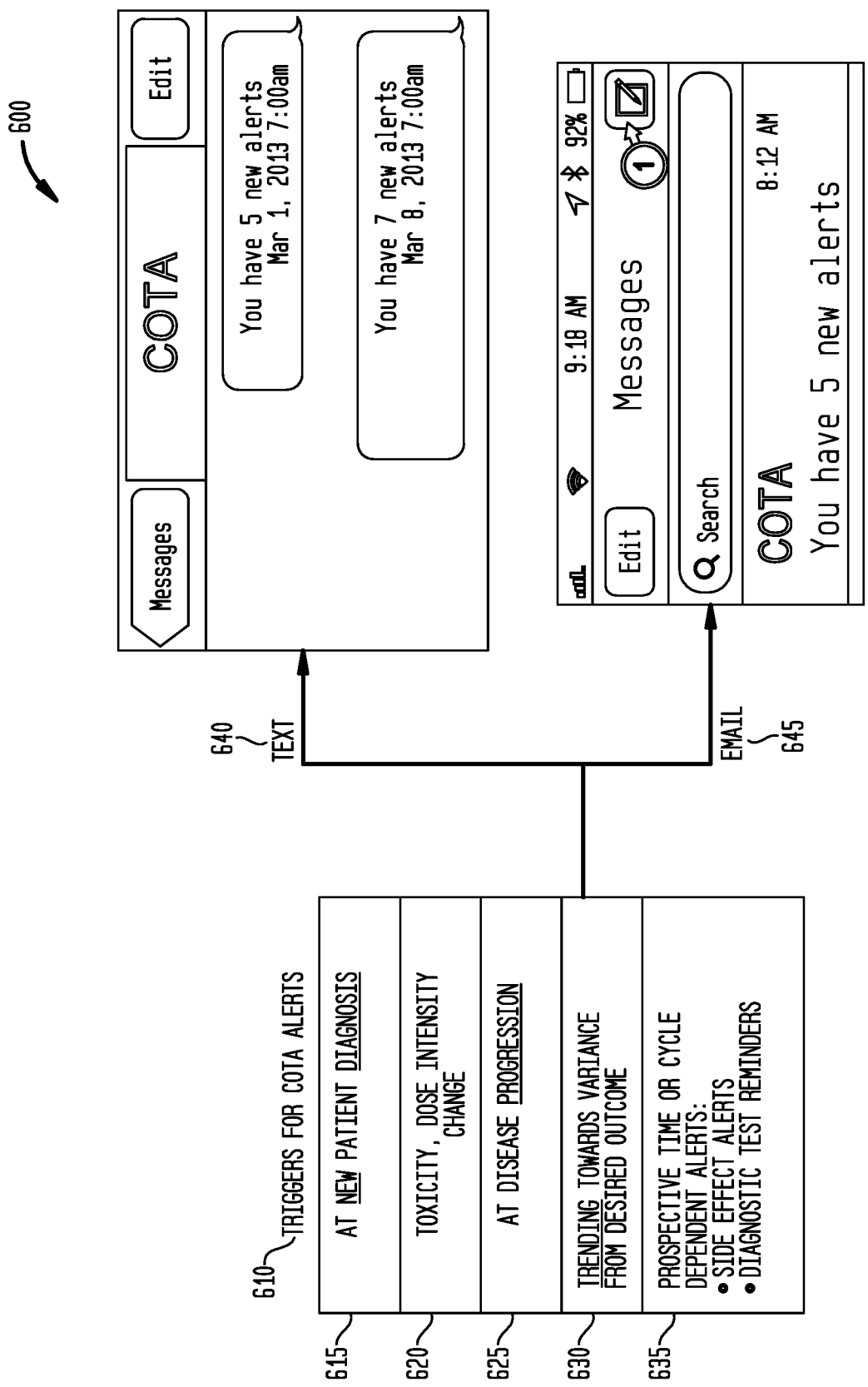
FIG. 6 illustrates a flow diagram of the COTA module transmitting alerts in response to triggers in accordance with an embodiment of the present disclosure.

FIG. 6 illustrates a flow diagram 600 of alerts provided by the COTA module 220 in accordance with an embodiment. In one embodiment, physicians or other medical professionals are alerted based on their preferences. These preferences can be set by the medical professional/physician and can include, for example, triggers 610 for the alerts and/or the technique used to provide the alert. A trigger for an alert can include, for example, at new patient diagnosis 615, an update to a diagnosis, real-time scheduled event, changes to group membership (e.g., a new gene identified which might change grouping, and/or someone leaving the group), toxicity and/or dose intensity change 620, at disease progression 625, administration of a particular drug, trending towards variance from desired outcome 630, and/or prospective time or cycle dependent alerts 635 (e.g., side effect alerts and/or diagnostic test reminders). The alert may include a text message 640 or an email 645 sent to the user computer 210. Other types of alerts are also contemplated, such as, e.g., a telephone call to the user computer 210, an update on a web page, a social media update, a message sent using, e.g., Twitter®, Facebook®, or other social media site, adding content to a software library or web page, and/or any other message or communication sent to or accessed by the user computer 210. Although described above as providing alerts, a trigger can be any action that results in the COTA module 220 performing any other action.

Figure 7:
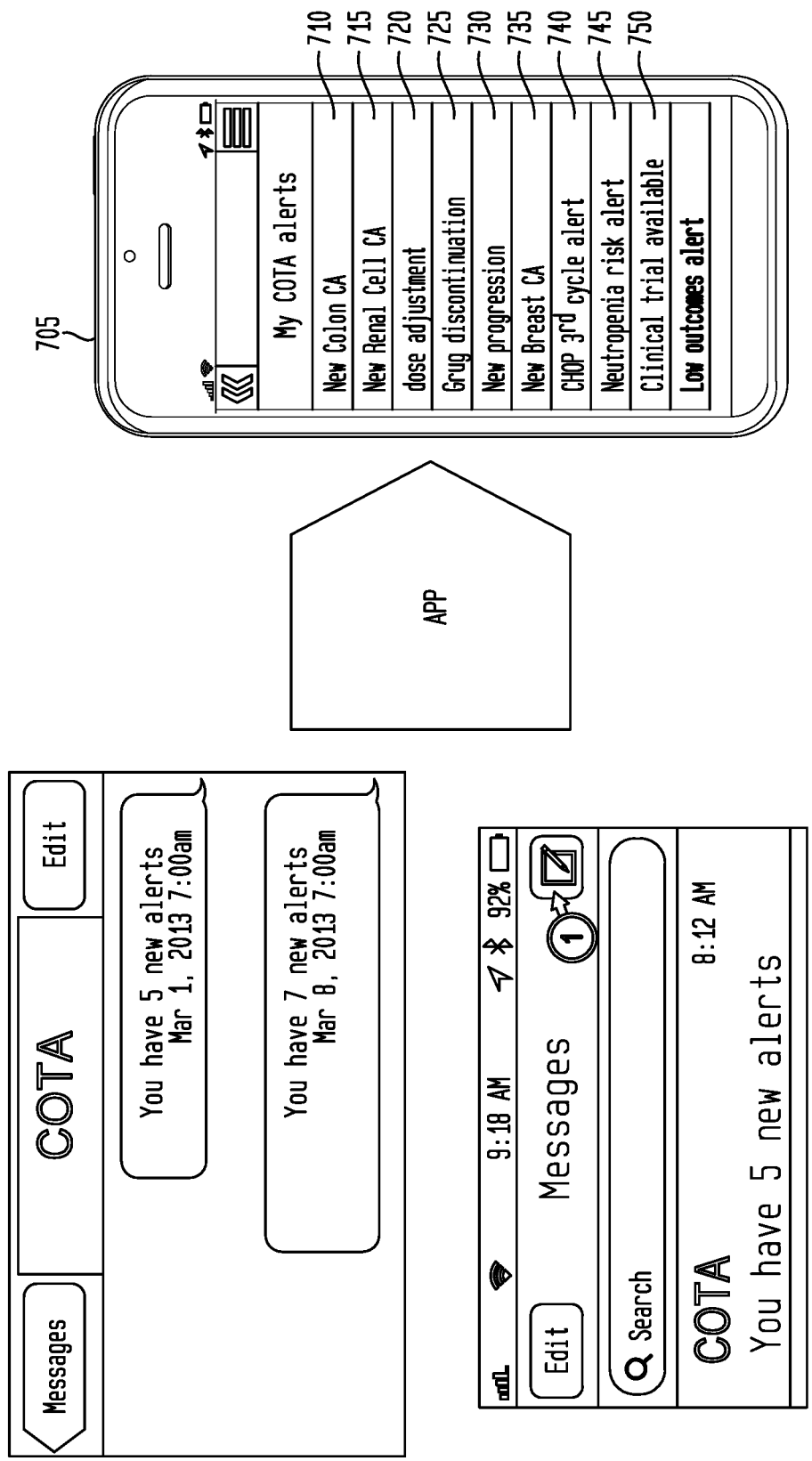
FIG. 7 is a graphical representation illustrating a mobile device organizing received alerts in accordance with an embodiment of the present disclosure.

FIG. 7 is a graphical representation illustrating a mobile device 705 (e.g., user computer 210) organizing alerts received by the device 705 in accordance with one embodiment. As shown in FIG. 7, the COTA alerts received are listed by a title or subject, such as New Colon CA 710, New Renal Cell CA 715, Dose Adjustment 720, Drug Discontinuation 725, New Progression 730, New Breast CA 735, CHOP $3^{rd}$ cycle alert 740, Neutropenia risk alert 745, and Clinical trial available 750. CHOP is an abbreviated name of a combination of drugs used in chemotherapy, which includes cyclophosphamide (Cytoxan/Neosar), doxorubicin (or Adriamycin), vincristine (Oncovin), and prednisolone, and is used, for example, to treat non-Hodgkin lymphoma.

The COTA module 220 can provide specific disease data sets (e.g., on demand and in real time) including, for instance, incidence of disease (e.g., by a COTA sort), progression free survival by progression status, and/or overall survival. In one embodiment, the COTA module 220 can provide a drug utilization data set, such as data associated with a full or partial therapy, toxicity, and/or a change in therapy.

Figure 8:
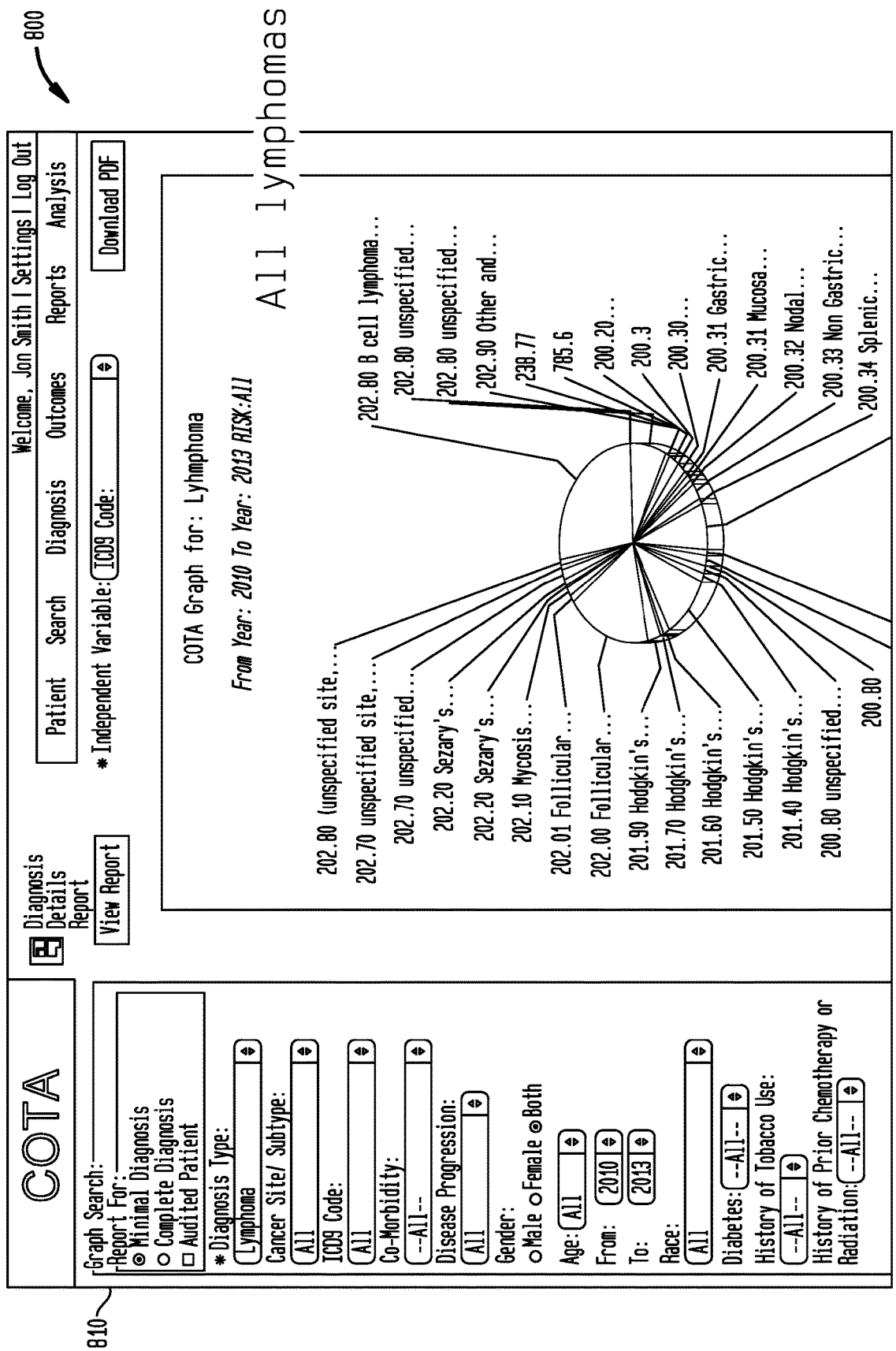
FIG. 8 shows a graphical representation of incidence of disease by cancer subtype in accordance with an embodiment of the present disclosure.

FIG. 8 shows a graphical representation 800 of incidence of disease by cancer subtype that can be provided by the COTA module 220 in accordance with one embodiment. Here, the COTA graph 800 is for lymphoma from years 2010 to 2013. A user can utilize a graph search input section 810 to narrow the information that is graphed. The graph search input section 810 can include, for example, a selection of what to report for (e.g., minimal diagnosis, complete diagnosis, and/or audited patient, diagnosis type, cancer site/subtype, ICD9 (International Classification of Diseases, Ninth Revision) code, Co-Morbidity, Disease Progression, Gender, Age, Date Range, Race, Diabetes, History of Tobacco Use, History of Prior Chemotherapy or Radiation, etc.

Figure 9:
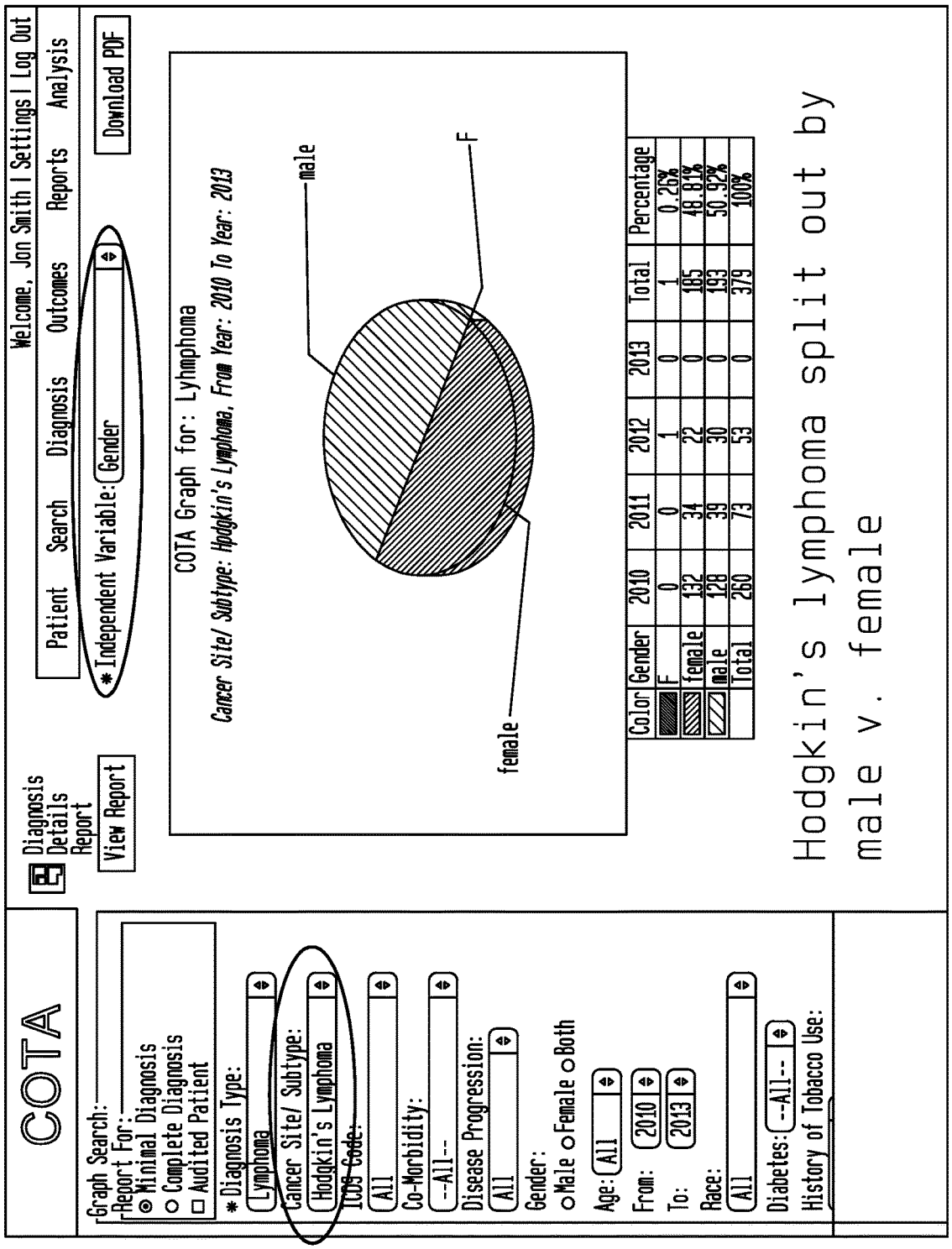
FIG. 9 is a graphical representation of a search refined by variables input into the COTA module in accordance with an embodiment of the present disclosure.

FIG. 9 shows a graphical representation 900 of a sort based on variables input into the COTA module 220 that can be provided by the COTA module 220 in accordance with one embodiment. The graphical representation 900 shows a COTA graph for Hodgkin's Lymphoma from years 2010-2013 split out by male vs. female. The graphical representation 900 shows statistics 910 of the different patients who had this disease that were graphed in representation 900.

FIG. 10 shows an exemplary listing of a plurality of variables 1005 pertinent to a particular disease (here, variables shown are for lymphoma) in accordance with one embodiment.

Figure 11:
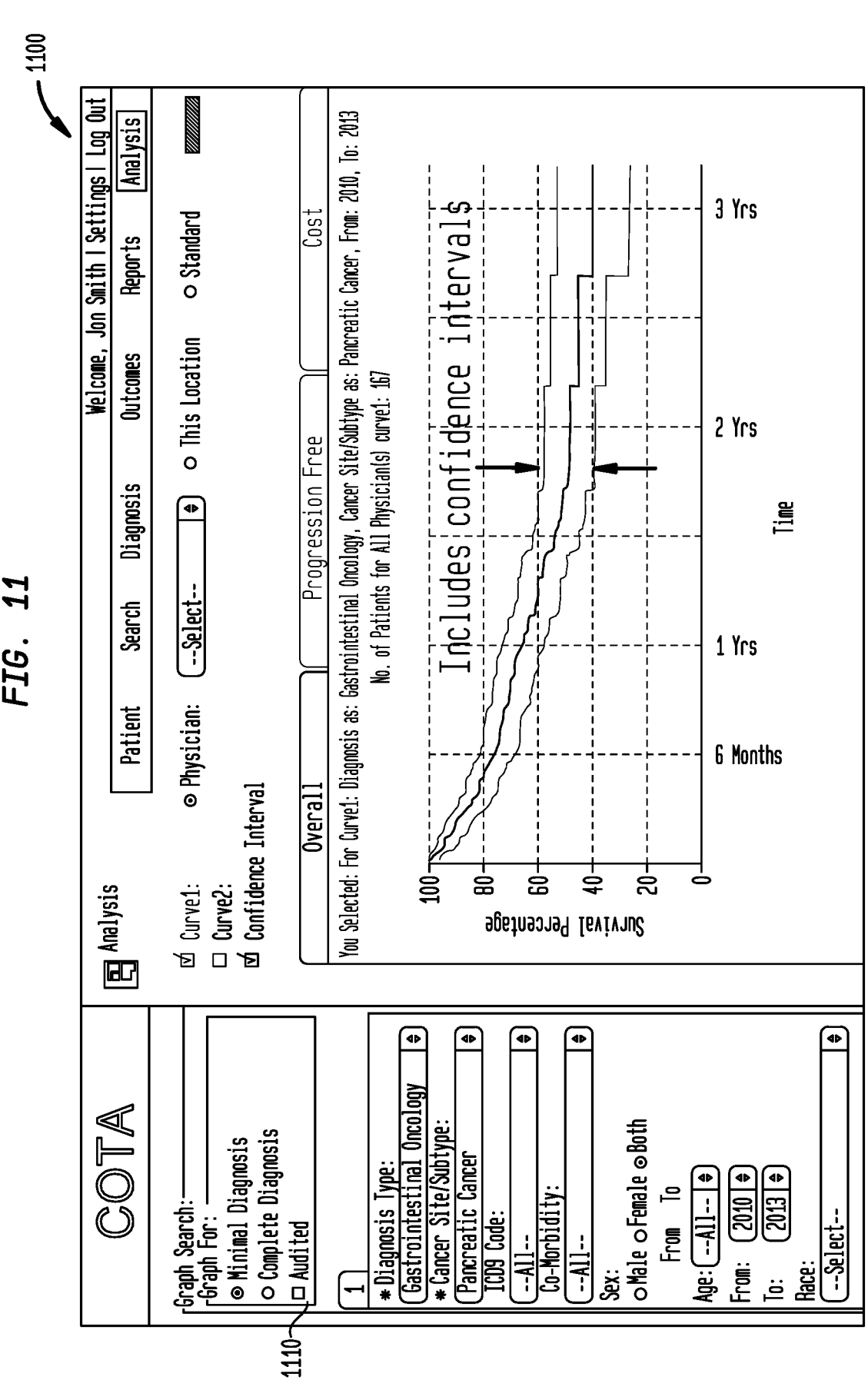
FIG. 11 shows a graphical representation including real-time Kaplan Meier curves with confidence intervals for pancreatic cancers in accordance with an embodiment of the present disclosure.

FIG. 11 shows a graphical representation 1100 including real-time Kaplan Meier curves with confidence intervals for pancreatic cancers that can be provided by the COTA module 220 in accordance with one embodiment. As described above, a Kaplan Meier curve is a curve that shows five year survival rate that can be developed, e.g., for a single doctor (or medical professional) or for a group of doctors (or medical professionals). A Kaplan Meier curve can be created for overall survival and/or progression free survival. The user indicates variables for his graph search in graph search input section 1110.

Figure 12:
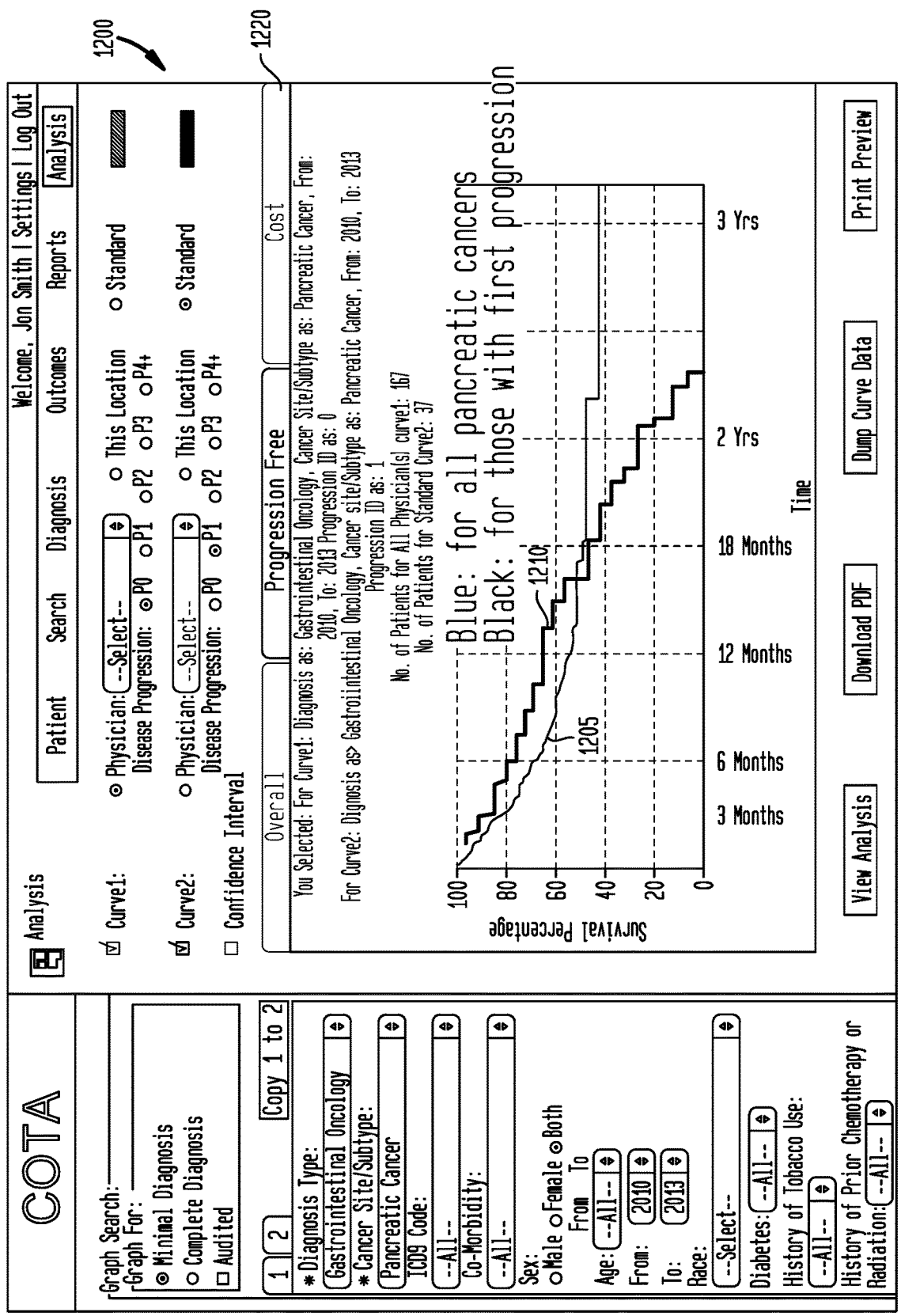
FIG. 12 is a graphical representation showing Kaplan Meier curves by disease progression in accordance with an embodiment of the present disclosure.

FIG. 12 is a graphical representation 1200 showing Kaplan Meier curves for disease progression that can be provided by the COTA module 220 in accordance with one embodiment. Line 1205 is for all pancreatic cancers, and bold line 1210 is for those with first progression.

Figure 13:
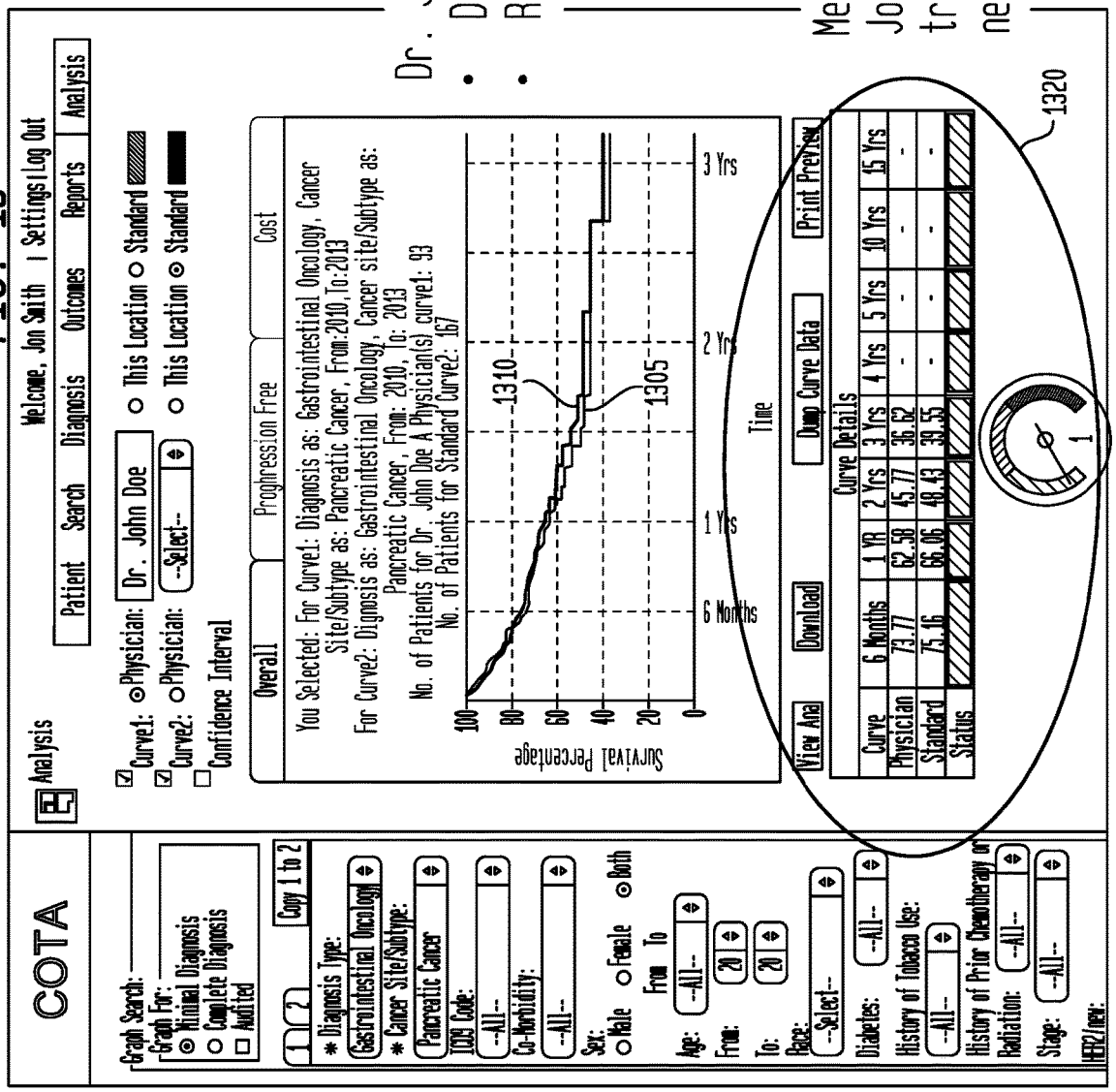
FIG. 13 is a graphical representation of real-time benchmarking of outcomes between two parties in accordance with an embodiment of the present disclosure.

FIG. 13 is a graphical representation 1300 of real time benchmarking of outcomes between two parties that can be provided by the COTA module 220 in accordance with one embodiment. The graph 1300 includes curve 1305 for outcomes of Dr. John Doe, a physician who treats pancreatic cancer, and a curve 1310 for outcomes of the rest of the doctors who treat pancreatic cancer. FIG. 13 also includes a meter 1320 measuring whether Dr. John Doe's outcomes are tracking positively or negatively.

Figure 14:
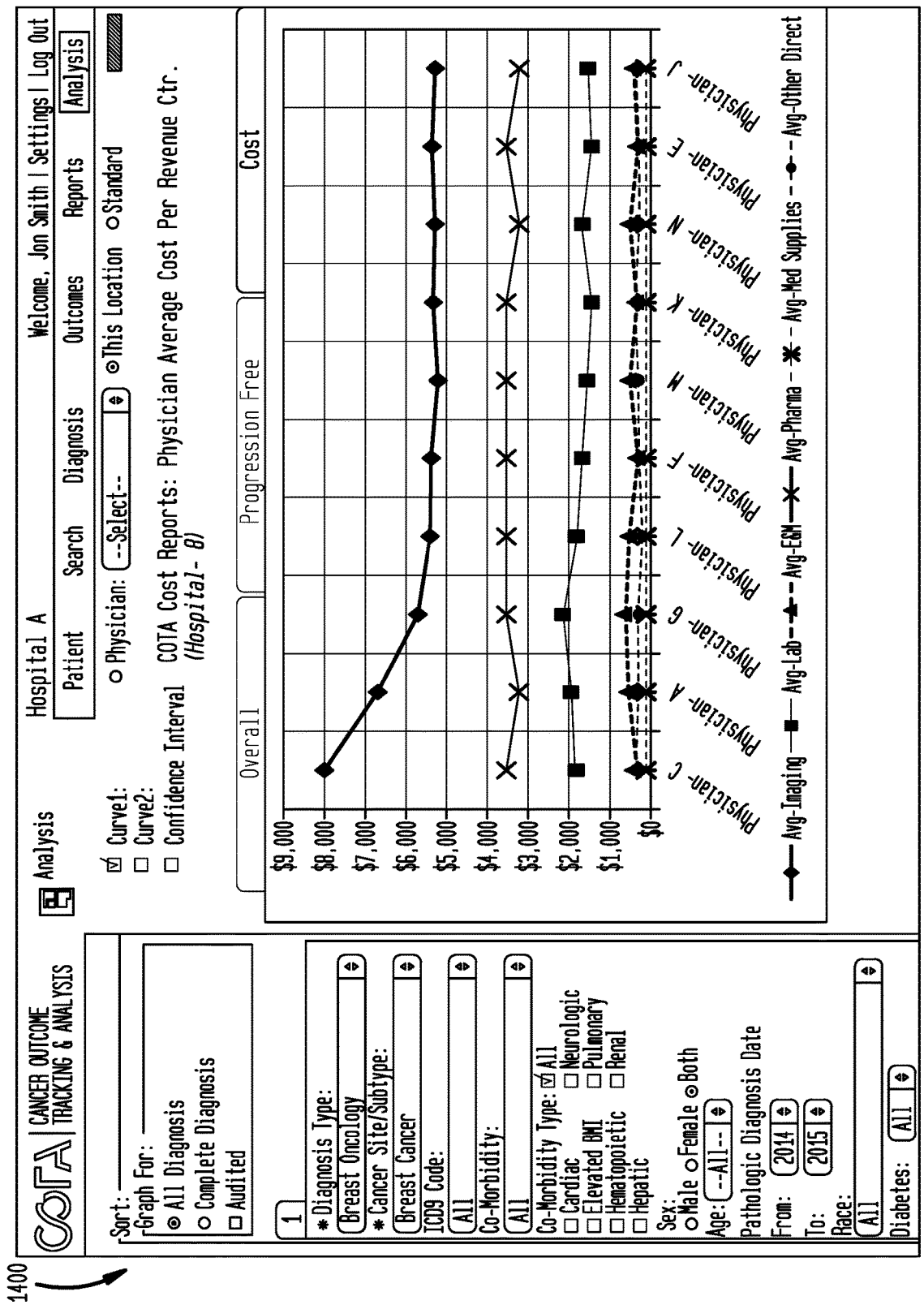
FIG. 14 is a graphical representation of a cost report in accordance with an embodiment of the present disclosure.

FIG. 14 is a graphical representation of a cost report 1400 associated with (e.g., provided by) the COTA module 220 in accordance with one embodiment. The screen's appearance is a result of the COTA nodal addresses (CNA) and its appearance can be changed however it is desired to present the information. The cost report 1400 may be associated with the cost tab 1220 of FIG. 12. The cost report 1400 can be used, for example, in estimating cost(s) of treatment, capturing knowledge, and/or transforming the knowledge into specific implementations. In one embodiment, the COTA module 220 tracks costs of various treatments, physicians, hospitals, etc. in real time. As shown in FIG. 14, the cost report 1400 illustrates a comparison between physician and average cost per revenue. Cost report 1400 may also include other comparisons, such as, e.g., hospital contribution margin in dollars and percent, hospital average revenue and cost (e.g., average revenue per patient, average cost per patient), physician average cost per case (e.g., average cost per case for each physician, weight peer average), physician average cost per revenue (e.g., average cost of imaging, lab work, evaluation and management, pharmaceuticals, medical supplies, and other expenses for each physician), etc.

FIGS. 15A and 15B are graphical representations of a treatment interface 1500 associated with (e.g., provided by) the COTA module 220 for facilitating the connection between outcomes and treatments, in accordance with one embodiment. As shown in FIG. 15A, the treatment interface 1500 may include a list the different types of treatment administered to (or declined by) a patient with breast cancer, such as, e.g., surgery, antineoplastic drugs, cellular therapy, radiation therapy, etc. Treatment may be arranged according to a disease progression. For example, drugs in oncology are typically given in cycles, and, in any one cycle, any number of drugs can be given. In one embodiment, a user can select a progression (e.g., represented as progression 0 to progression 4), with progression 0 being after first diagnosis, cycle, and can select drugs in or from multiple categories.

In FIG. 15B, in another embodiment, a treatment interface 1510 may include treatment regimens for one or more therapies, graphically represented on treatment interface 1510 as tabs 1515. Treatment interface 1510 may include fields to indicate a start and end data for the regimen, dose intensity, description of treatment, specific brands of drugs, etc. Treatment regimens may be graphically summarized or represented as a listing of treatments in table 1520. Table 1520 may include action icons 1505 for each treatment. The action icons 1505 may facilitate actions, such as, e.g., editing, closing, viewing components, etc. In one embodiment, the action icons 1505 may be shortcuts to perform complex tasks (e.g., requiring multiple clicks or selections) with a single selection. For example, an icon on the diagnosis line can bring the user to the diagnosis screen.

FIG. 16 is a graphical representation of an outcome screen 1600 for facilitating outcome tracking in accordance with one embodiment. Outcome screen 1600 may facilitate outcome tracking from, for example, diagnosis (i.e., progression zero), first progression, second progression through fourth progression, with each progression considered a different disease. The outcome screen tab can include (e.g., in one or more drop down menus or other fields) a diagnosis date, a treatment start and end date, a response to treatment (e.g., complete, partial, stable) and date of response, input fields for notes on the response (e.g., the partial field, CR-RA-Pet Negative field, the CR field, etc.), and a track end data, which may include fields for last contact and death. The outcome screen 1600 may also include other fields, such as, e.g., toxicity of a drug treatment, an input area enabling the input of what happened (e.g., discontinued, continued, no change, drug dosage change, and how many times), number of delays, number changes in drug, and/or number reduced. In one embodiment, a user of the COTA module 220 can flag a patient.

Figure 17:
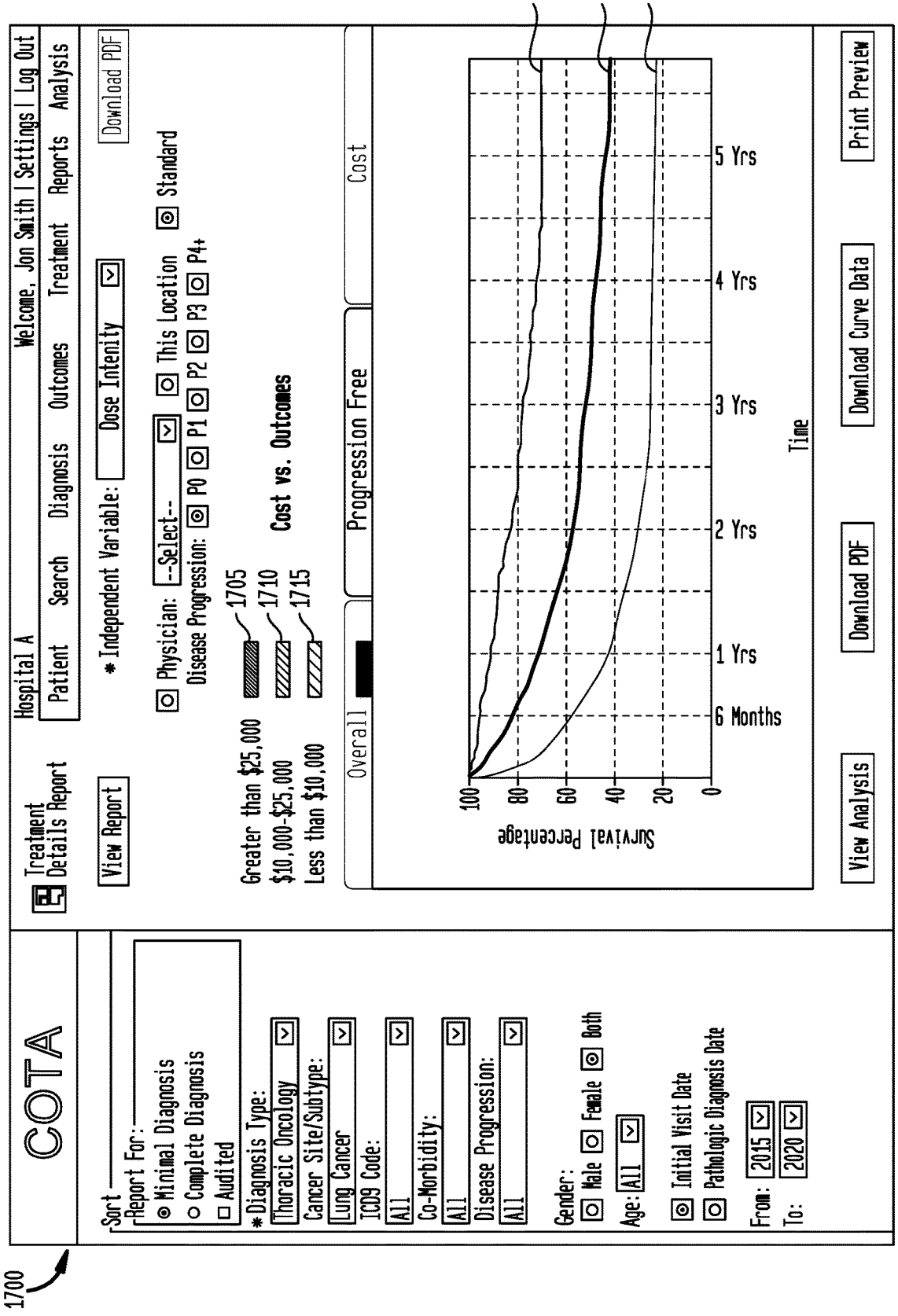
FIG. 17 is a graphical representation of a treatment details report screen in accordance with an embodiment of the present disclosure.

FIG. 17 is a graphical representation of a treatment details report screen 1700 illustrating a comparison between cost and outcome in accordance with one embodiment. The treatment details report screen 1700 correlates cost of care to clinical outcome to optimize value of care. Cost and financial data may be collected and analyzed by hospital, by doctor, etc. over a given time period (e.g., 5 years). The cost and financial data may be represented in one or more ranges of cost. In one embodiment, the ranges of cost include range 1705 for cost greater than $25,000, range 1710 for cost from $10,000 to $25,000, and range 1715 for cost less than $10,000. When combined with clinical data, the COTA module 220 may provide cost data for different treatments for a given time period based on different clinical sorts.

Figure 18:
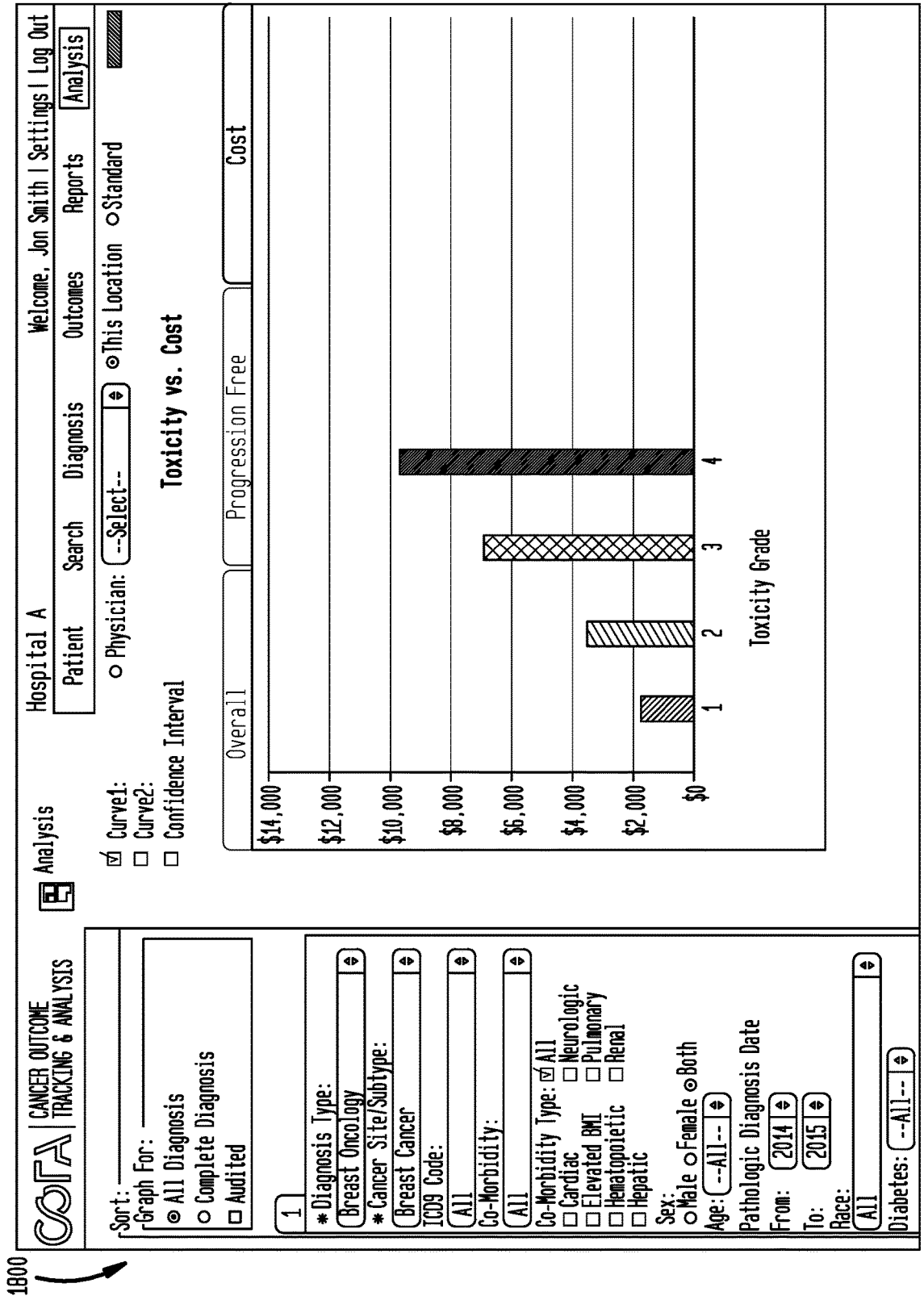
FIG. 18 is a graphical representation of an analysis screen comparing toxicity and cost in accordance with an embodiment of the present disclosure.

FIG. 18 is a graphical representation of an analysis screen 1800 provided by the COTA module 220 illustrating a comparison between toxicity and cost in accordance with one embodiment. The screen's appearance is a result of the COTA nodal addresses (CNA) and its appearance can be changed however it is desired to present the information. The analysis screen 1800 correlates incidence and severity of toxicity to cost of care and outcomes of care. The toxicity may be represented numerically (e.g., in ranges), by standards (e.g., grades), etc. For example, as shown in FIG. 18, toxicity is represented as toxicity grades 1-4 based on the Common Terminology Criteria for Adverse Events (CT-CAE) classification. The grade of toxicity is graphically compared with cost. The analysis screen 1800 may be used to optimize value and efficacy of care, where value is efficacy/cost. In one embodiment, the COTA module 220 attempts to obtain high efficacy and low cost.

Figure 19:
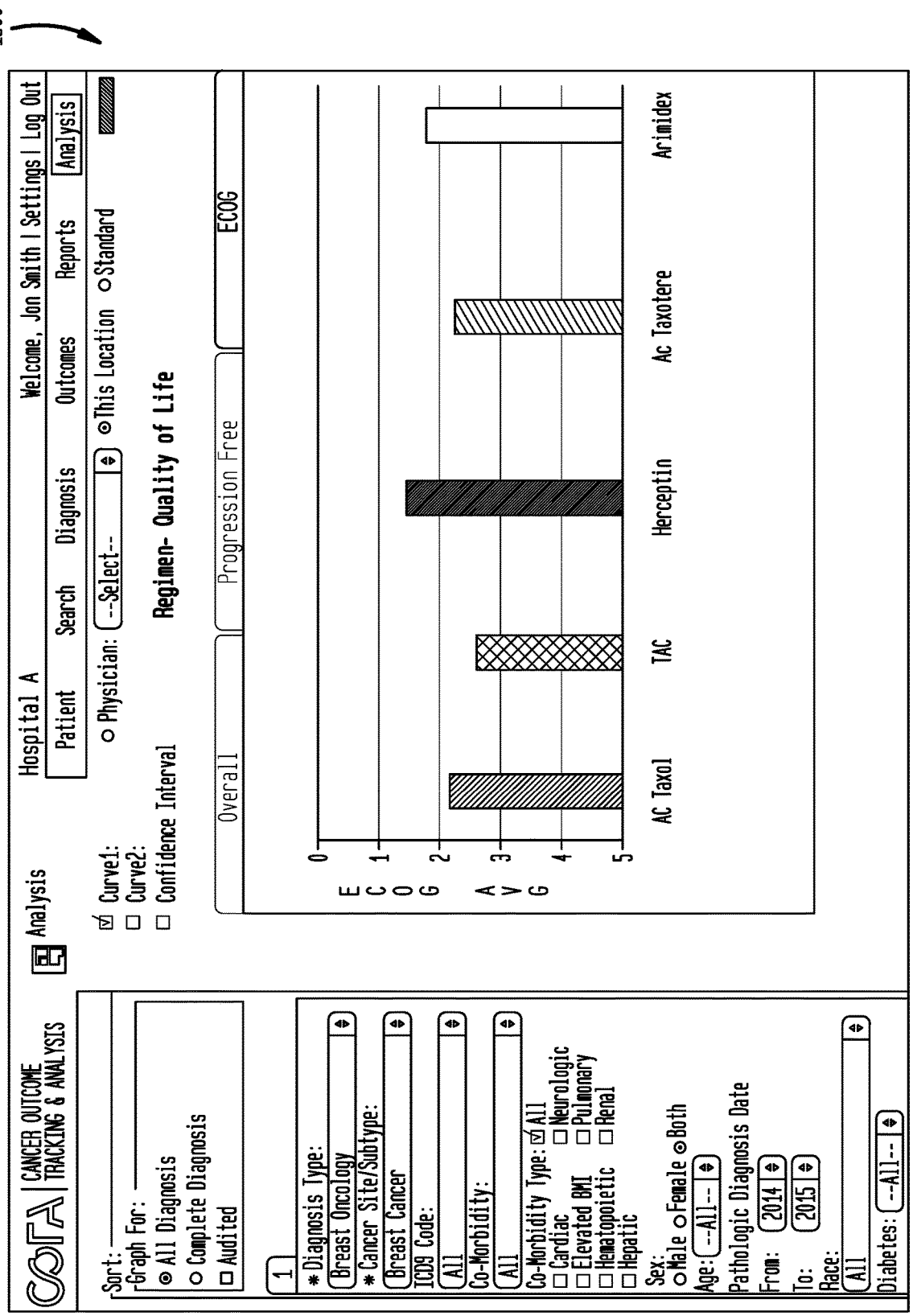
FIG. 19 is a graphical representation of an analysis screen comparing therapy and quality of life in accordance with an embodiment of the present disclosure.

FIG. 19 is a graphical representation of an analysis screen 1900 provided by the COTA module 220 illustrating a comparison between therapy and quality of life in accordance with one embodiment. The therapy may be represented by treatment drugs in analysis screen 1900. However, other forms of therapy are also contemplated, such as, e.g., surgery, procedures, etc. In one embodiment, the therapy includes an incidence, severity, and toxicity of therapy. Quality of life may be measured based on the average ECOG (Eastern Cooperative Oncology Group) scale, ranging from Grade 0 (i.e., fully active) to Grade 5 (i.e., dead). Quality of life may also be measured using any suitable metric. Analysis screen 1900 may facilitate assessment of how a patient's disease is progressing, how the disease affects the daily living abilities of the patient, and appropriate treatments and prognoses.

Figure 20:
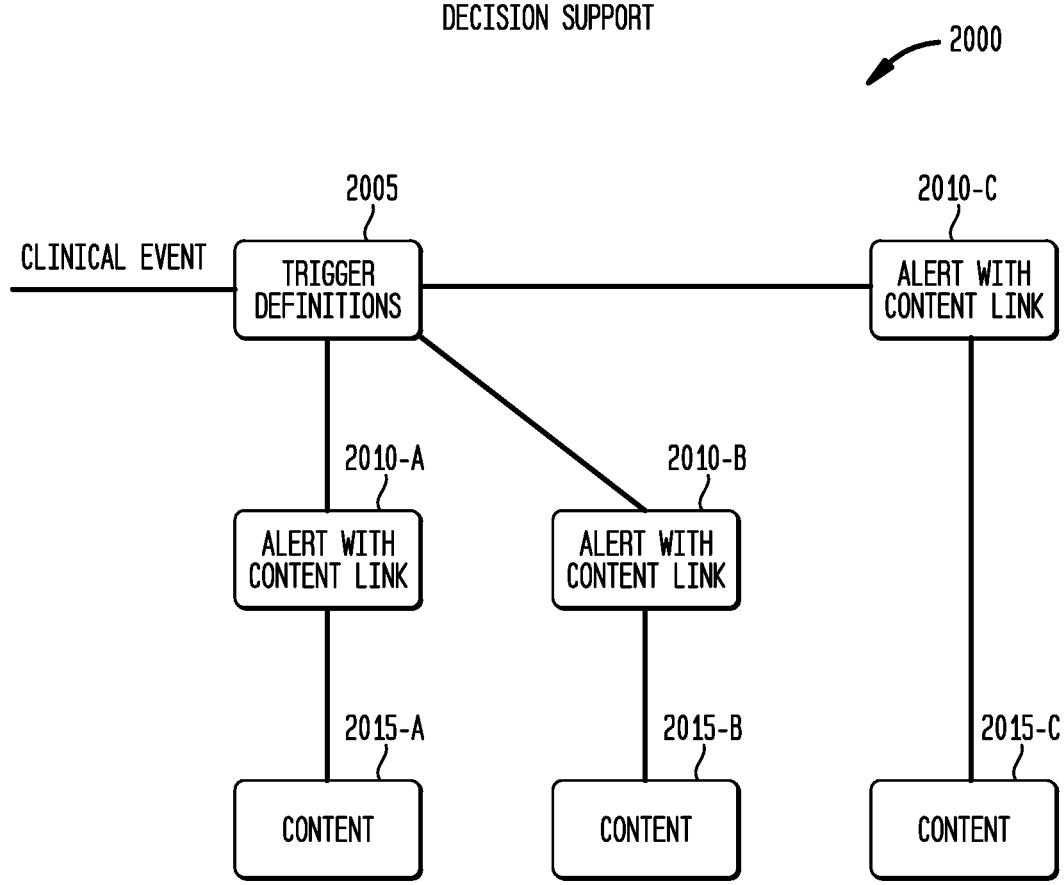
FIG. 20 is a flow diagram of feedback support provided to a medical professional in accordance with an embodiment of the present disclosure.

FIG. 20 is a flow diagram 2000 illustrating the alert system provided to a medical professional in accordance with one embodiment. The screen's appearance is a result of the COTA nodal addresses (CNA) and its appearance can be changed however it is desired to present the information. In one embodiment, the information in the alert is helping the user to make a decision in the future. In one embodiment, the information in the alert is providing a set of attributes that happened in the past time period. In one embodiment, it is both proactively influencing decisions of the user and reactively providing a digest report of how the medical personnel/Doctor did in the past week, month, quarter, etc. In one embodiment, there are different alerts for different users, each of which can influence decisions that the user makes. The alert may be employed for real time course correction to drive best value, such as, e.g., where an administered therapy deviates from a desired outcome. In block 2005, definitions are triggered based on clinical data. The definitions may be triggered using any criteria, such as, e.g., new disease diagnosis, disease progression, patient response, change in patient characteristics, dose change/drug toxicity change, trend towards variance from a desire outcome, etc. The criteria may be adjusted based on the disease and its parameters. Based on the triggered definitions, alerts 2010-A, 2010-B, 2010-C (collectively referred to as alerts 2010) are transmitted. It should be understood that alerts 2010 may include any number of alerts. The alerts 2010 may include content or a link to content. The alerts 2010 may be transmitted to the responsible physician, other medical professionals, hospital, pharmaceutical company, or any other person or entity.

Content 2015-A, 2015-B, 2015-C (collectively referred to as content 2015) is displayed, e.g., using user computer 210 to provide the alert. The content 2015 may include the patient data associated with the alert 2010, a comparison, or any other relevant content. In one embodiment, the comparison may be, e.g., between physicians, between one physician's patients and the whole patient population, between one physician and all physicians at a particular location, etc. The comparison may be based on a trending analysis to show where treatment is trending and if it is going off course (i.e., results are not as good as the standard). The comparison may be graphically displayed as one or more curves on a graph. In one embodiment, the COTA module 220 is utilized with cloud-based computing. The COTA module 220 can also enable or utilize connectivity to hospital records.

In one embodiment, the content 2015 may include feedback support to the medical professional having traffic light feedback indicators (not shown) on a display. For example, blue may mean very good performance (i.e., better than standard), green may mean standard performance, yellow may mean sufficient performance but may need to pay attention, red may mean the user may need to pay attention to something regarding the medical professional's approach to this disease. Other implementations of feedback indicators may also be employed.

FIGS. 21-24 show graphical representations for different diagnosis types in accordance with one or more embodiments. FIG. 21 shows a diagnosis screen 2100 for gastrointestinal oncology (e.g., colon cancer). FIG. 22 shows a diagnosis screen 2200 for breast oncology (e.g., breast cancer). FIG. 23 shows a diagnosis screen 2300 for thoracic oncology (e.g., lung cancer). Diagnosis screens 2100, 2200, 2300 include a number of different parameters, such as tests or aspects of the disease. The parameters may be represented as simple indicators, numerically based parameters, standards based parameters, etc.

Figure 24:
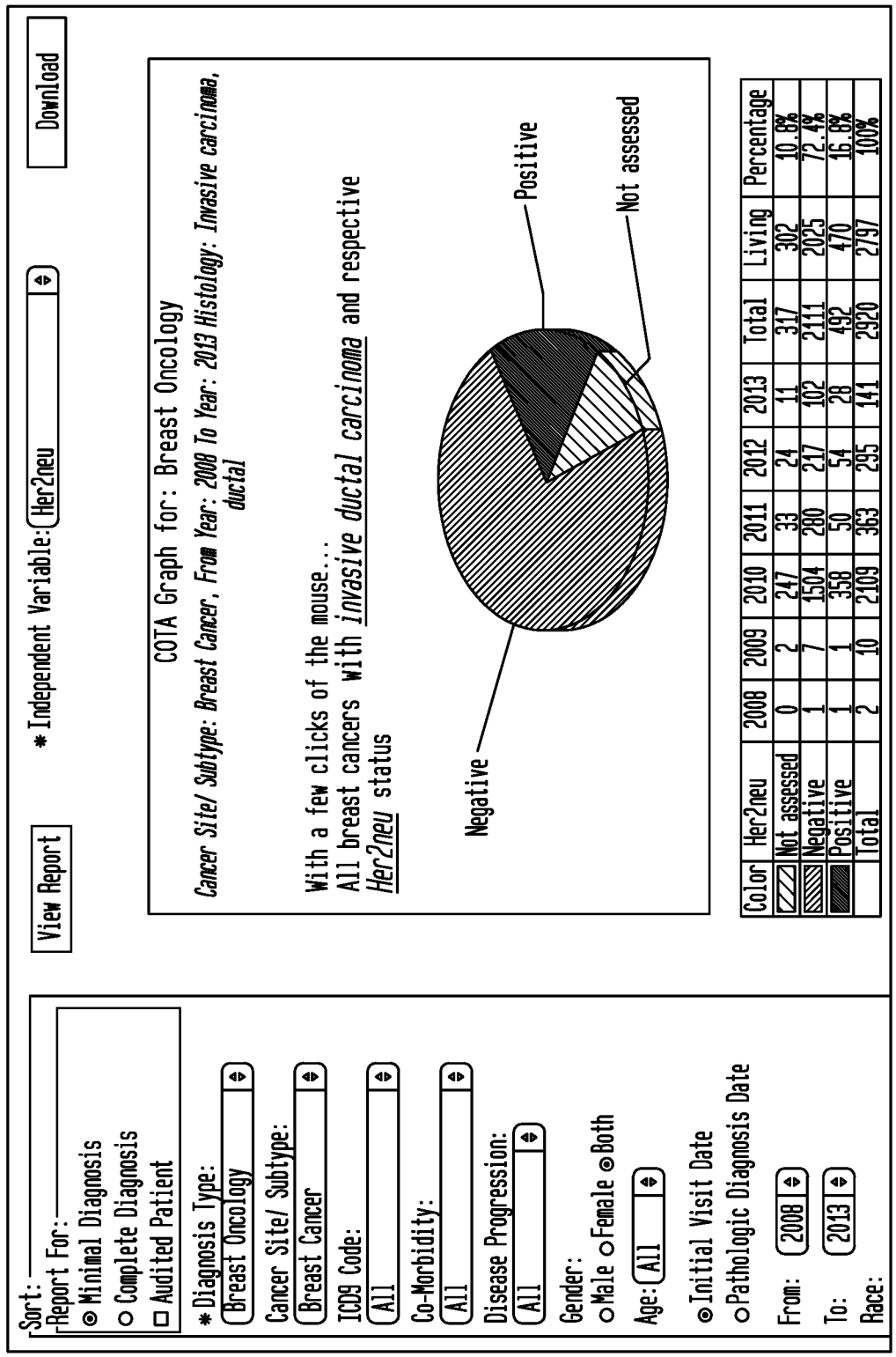
FIG. 24 shows a graphical representation illustrating the COTA module's data generation and sorting for breast oncology—breast cancer from year 2008 to year 2013 histology with invasive ductal carcinoma in accordance with an embodiment of the present disclosure.

FIG. 24 shows a graphical representation of a reporting screen 2400 illustrating the COTA module 220's data generation and sorting for breast oncology. Reporting screen 2400 shows breast cancer from year 2008 to year 2013 by histology, i.e., with invasive ductal carcinoma, in accordance with one embodiment. The reporting screen 2400 permits selection of breast cancer patients based on stage, age, progression, or any other parameter in real time. Advantageously, reporting screen 2400 allows categorization in a clinically relevant way.

Figure 25:
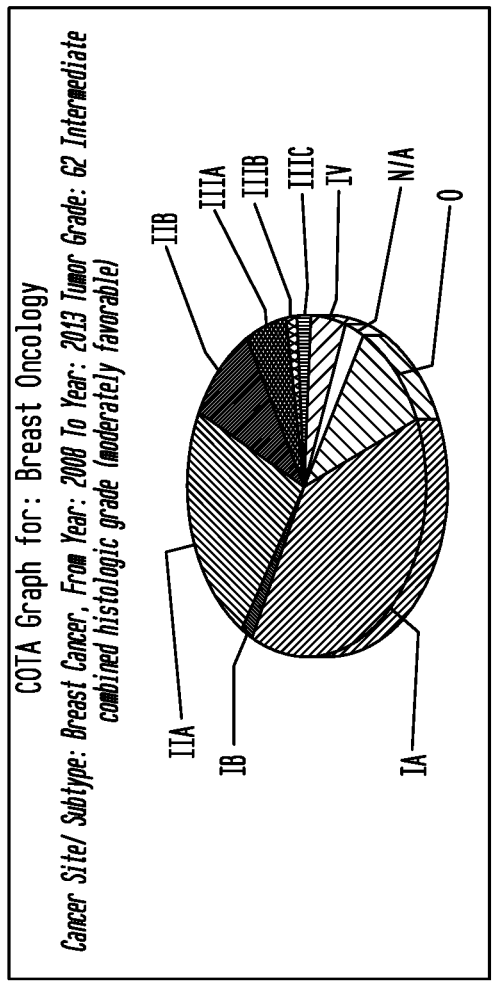
FIG. 25 shows a graphical representation illustrating the COTA module's data generation and sorting for breast oncology—breast cancer from year 2008 to year 2013 tumor grade and stage in accordance with an embodiment of the present disclosure.

FIG. 25 shows a graphical representation of a reporting screen 2500 illustrating the COTA module 220's data generation and sorting for breast oncology. Reporting screen 2500 shows all grade 2 breast cancer from year 2008 to year 2013 tumor by stage, in accordance with one embodiment.

Figure 26:
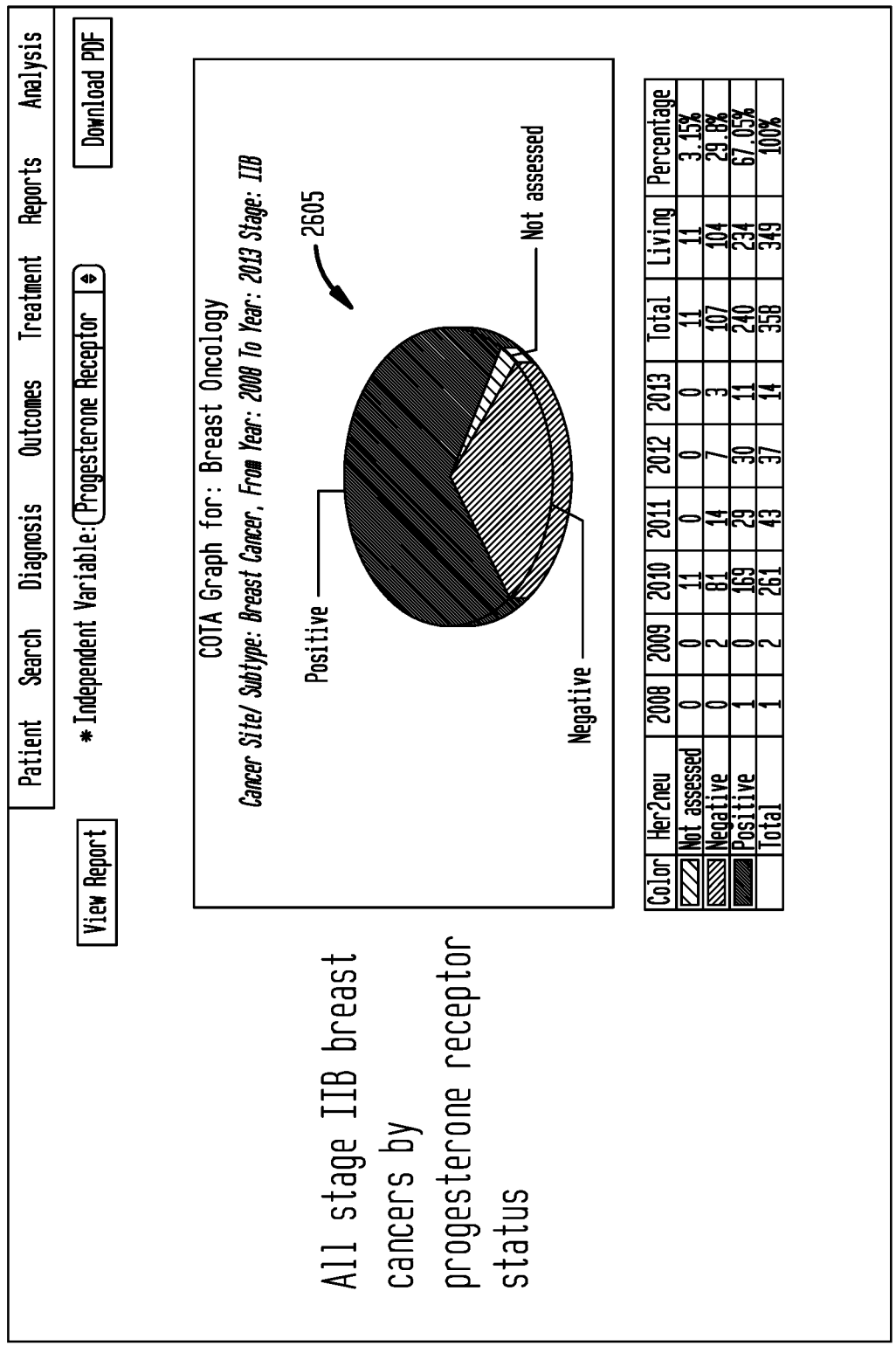
FIG. 26 shows a graphical representation illustrating the COTA module's data generation and sorting for breast cancer—stage IIB from year 2008 to 2013 in accordance with an embodiment of the present disclosure.

FIG. 26 shows a graphical representation of a reporting screen 2600 illustrating the COTA module 220's data generation and sorting for breast cancer. Reporting screen 2600 shows all stage IIB breast cancers from year 2008 to 2013, in accordance with one embodiment. Graph 2605 on reporting screen 2600 shows all stage IIB breast cancers by progesterone receptor status.

Figure 27:
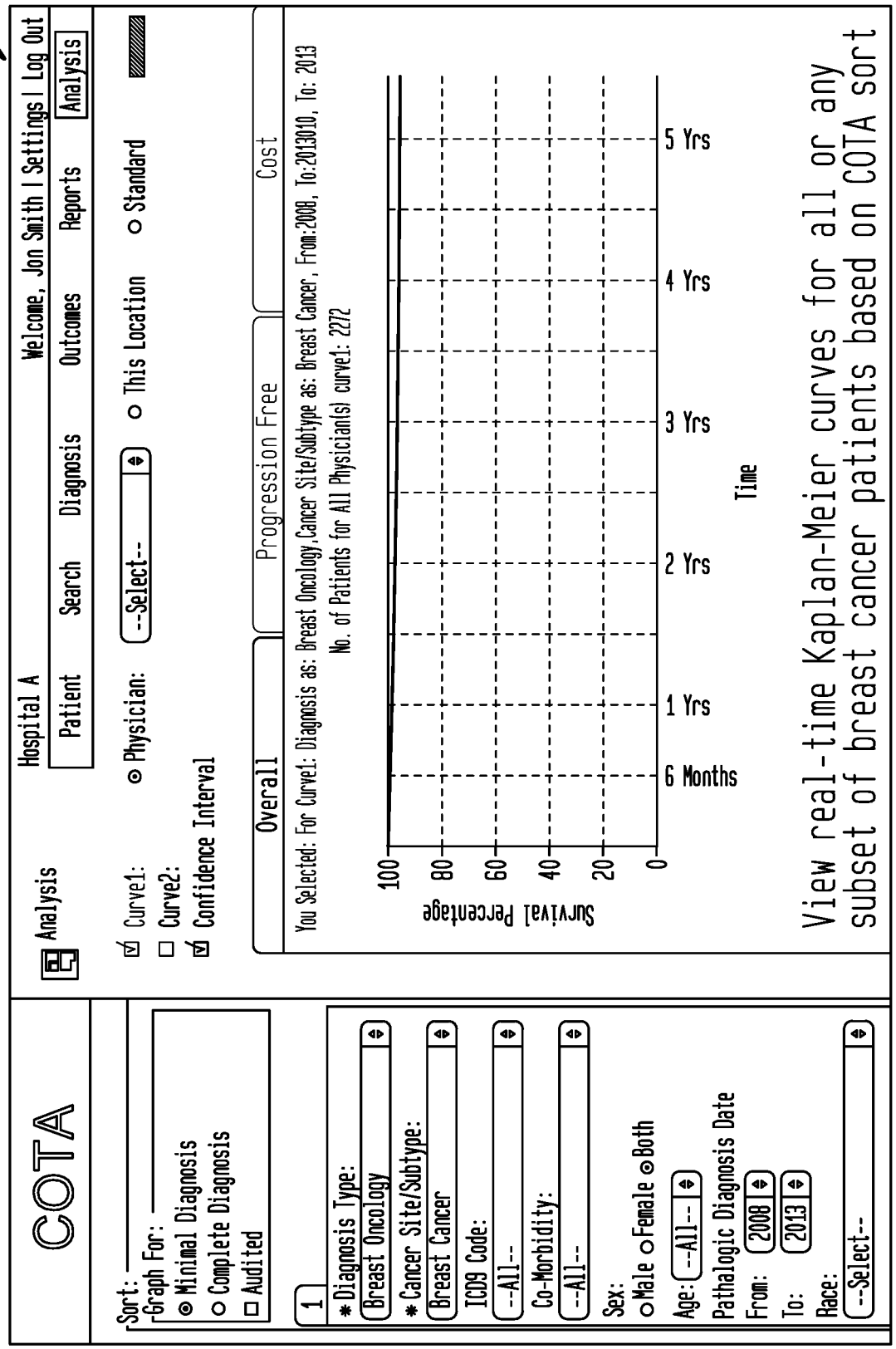
FIG. 27 shows a graphical representation illustrating overall survival outcomes for breast cancer patients in accordance with an embodiment of the present disclosure.
Figure 28:
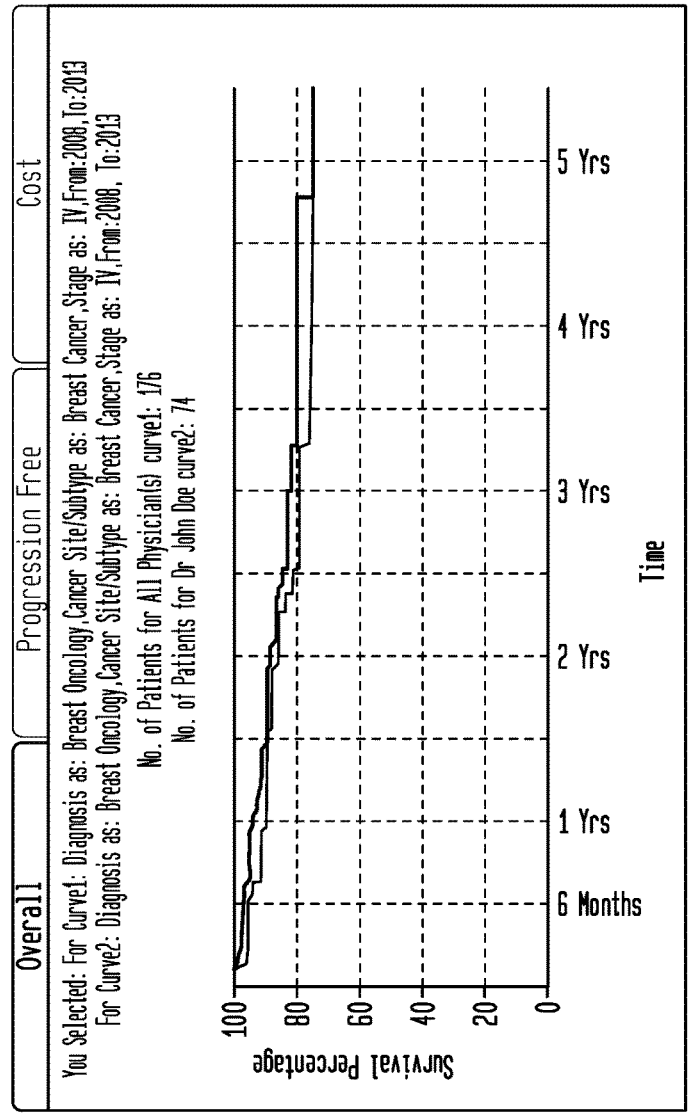
FIG. 28 shows a graphical representation illustrating outcomes for breast cancer—a comparison between two parties in accordance with an embodiment of the present disclosure.

FIG. 27 shows a graphical representation of an analysis screen 2700 illustrating overall survival outcomes for breast cancer patients in accordance with one embodiment. FIG. 28 shows a graphical representation 2800 illustrating survival outcomes for breast cancer as a comparison between Dr. John Doe (bold line) and the aggregate (non-bold line) parties, in accordance with one embodiment.

In one embodiment, the "node" described above represents every possible permutation of the variables shown in one or more of the graphical representations (e.g., in one or more of FIGS. 21-27).

Figure 29:
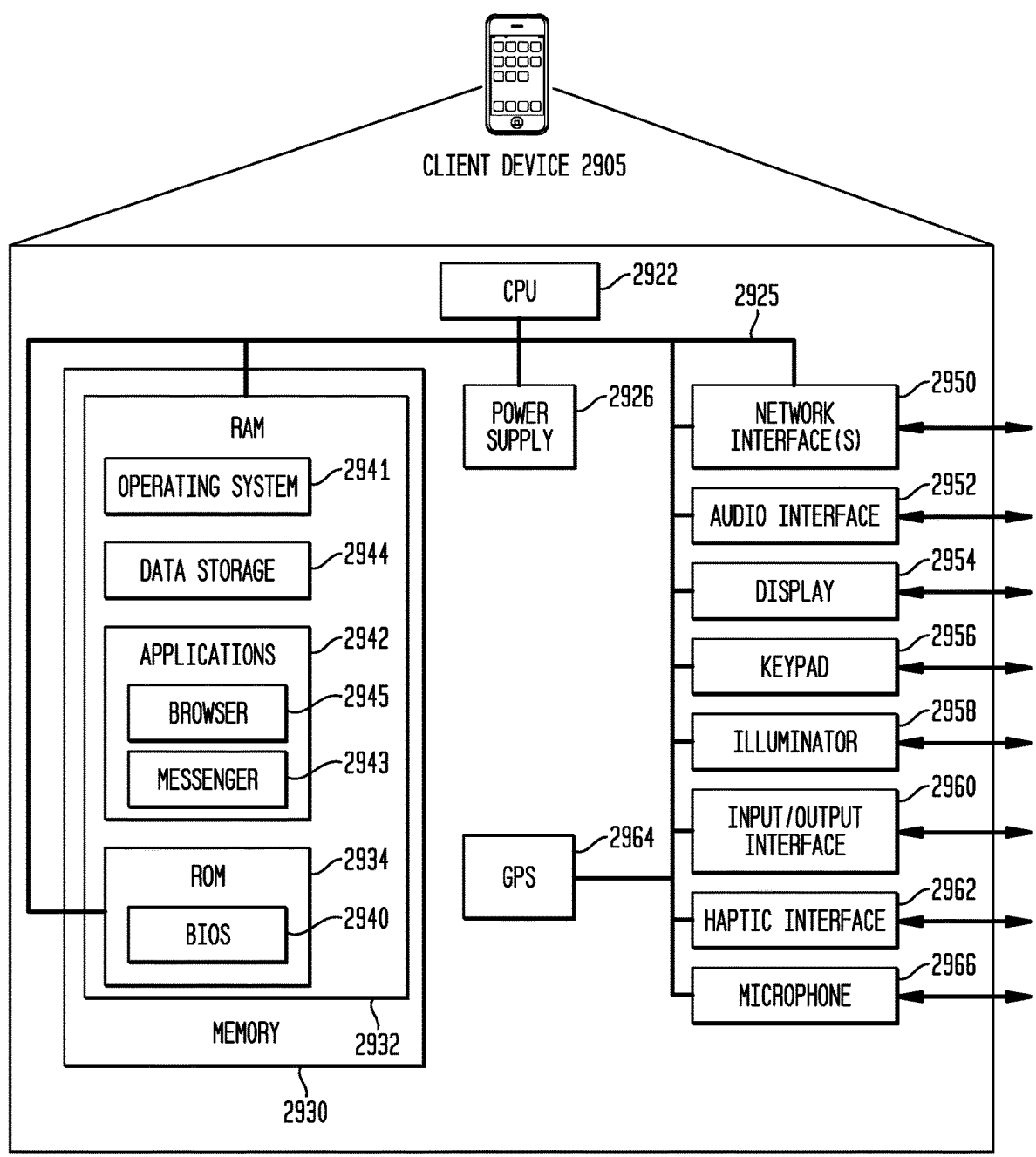
FIG. 29 depicts one example of a schematic diagram illustrating a client device in accordance with an embodiment of the present disclosure.

As shown in the example of FIG. 29, client device 2905 may include one or more processing units (also referred to herein as CPUs) 2922, which interface with at least one computer bus 2925. Client device 2905 may be, for example, user computer 210. A memory 2930 can be persistent storage and interfaces with the computer bus 2925. The memory 2930 includes RAM 2932 and ROM 2934. ROM 2934 includes a BIOS 2940. Memory 2930 interfaces with computer bus 2925 so as to provide information stored in memory 2930 to CPU 2922 during execution of software programs such as an operating system 2941, application programs 2942, device drivers, and software modules 2943, 2945 that comprise program code, and/or computer-executable process steps, incorporating functionality described herein, e.g., one or more of process flows described herein. CPU 2922 first loads computer-executable process steps from storage, e.g., memory 2932, data storage medium/media 2944, removable media drive, and/or other storage device. CPU 2922 can then execute the stored process steps in order to execute the loaded computer-executable process steps. Stored data, e.g., data stored by a storage device, can be accessed by CPU 2922 during the execution of computer-executable process steps.

Persistent storage medium/media 2944 is a computer readable storage medium(s) that can be used to store software and data, e.g., an operating system and one or more application programs. Persistent storage medium/media 2944 can also be used to store device drivers, such as one or more of a digital camera driver, monitor driver, printer driver, scanner driver, or other device drivers, web pages, content files, playlists and other files. Persistent storage medium/media 2206 can further include program modules and data files used to implement one or more embodiments of the present disclosure.

For the purposes of this disclosure a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Client device 2905 can also include one or more of a power supply 2926, network interface 2950, audio interface 2952, a display 2954 (e.g., a monitor or screen), keypad 2956, illuminator 2958, I/O interface 2960, a haptic interface 2962, a GPS 2964, a microphone 2966, a video camera, TV/radio tuner, audio/video capture card, sound card, analog audio input with A/D converter, modem, digital media input (HDMI, optical link), digital I/O ports (RS232, USB, FireWire, Thunderbolt), expansion slots (PCMCIA, ExpressCard, PCI, PCIe).

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium. Modules may be integral to one or more servers, or be loaded and executed by one or more servers. One or more modules may be grouped into an engine or an application.

Figure 30:
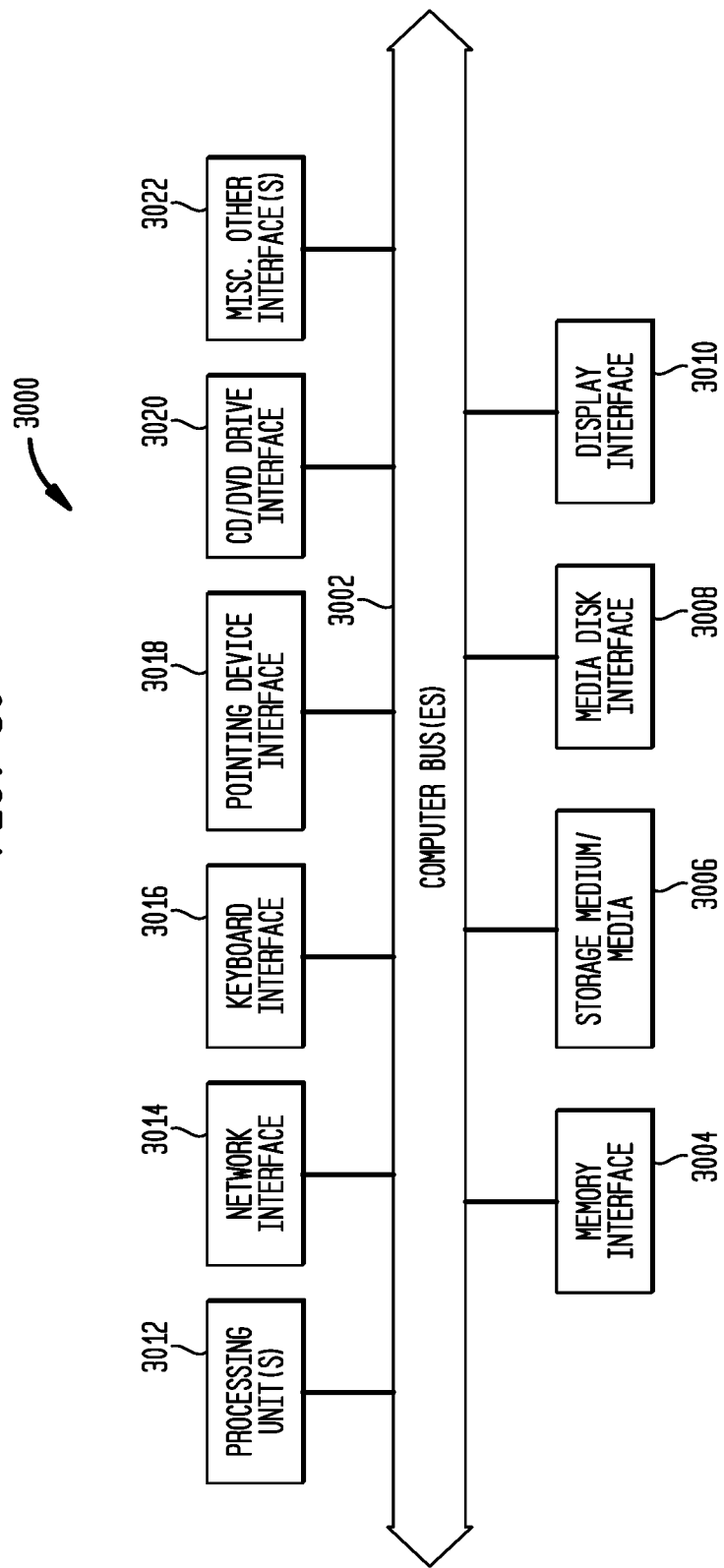
FIG. 30 is a block diagram illustrating an internal architecture of a computer in accordance with an embodiment of the present disclosure.

FIG. 30 is a block diagram illustrating an internal architecture of an example of a computer, such as server computer 205 and/or user computer 210, in accordance with one or more embodiments of the present disclosure. A computer as referred to herein refers to any device with a processor capable of executing logic or coded instructions, and could be a server, personal computer, set top box, tablet, smart phone, pad computer or media device, to name a few such devices. As shown in the example of FIG. 30, internal architecture 3000 includes one or more processing units (also referred to herein as CPUs) 3012, which interface with at least one computer bus 3002. Also interfacing with computer bus 3002 are persistent storage medium/media 3006, network interface 3014, memory 3004, e.g., random access memory (RAM), run-time transient memory, read only memory (ROM), etc., media disk drive interface 2308 as an interface for a drive that can read and/or write to media including removable media such as floppy, CD-ROM, DVD, etc. media, display interface 3010 as interface for a monitor or other display device, keyboard interface 3016 as interface for a keyboard, pointing device interface 3018 as an interface for a mouse or other pointing device, and miscellaneous other interfaces not shown individually, such as parallel and serial port interfaces, a universal serial bus (USB) interface, and the like.

Memory 3004 interfaces with computer bus 3002 so as to provide information stored in memory 3004 to CPU 3012 during execution of software programs such as an operating system, application programs, device drivers, and software modules that comprise program code, and/or computer-executable process steps, incorporating functionality described herein, e.g., one or more of process flows described herein. CPU 3012 first loads computer-executable process steps from storage, e.g., memory 3004, storage medium/media 3006, removable media drive, and/or other storage device. CPU 3012 can then execute the stored process steps in order to execute the loaded computer-executable process steps. Stored data, e.g., data stored by a storage device, can be accessed by CPU 3012 during the execution of computer-executable process steps.

As described above, persistent storage medium/media 3006 is a computer readable storage medium(s) that can be used to store software and data, e.g., an operating system and one or more application programs. Persistent storage medium/media 3006 can also be used to store device drivers, such as one or more of a digital camera driver, monitor driver, printer driver, scanner driver, or other device drivers, web pages, content files, playlists and other files. Persistent storage medium/media 3006 can further include program modules and data files used to implement one or more embodiments of the present disclosure.

Internal architecture 3000 of the computer can include (as stated above), a microphone, video camera, TV/radio tuner, audio/video capture card, sound card, analog audio input with A/D converter, modem, digital media input (HDMI, optical link), digital I/O ports (RS232, USB, FireWire, Thunderbolt), and/or expansion slots (PCMCIA, Express-Card, PCI, PCIe).

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the user computing device or server or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

While the system and method have been described in terms of one or more embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A method for clinical outcome tracking and analysis comprising:

accessing or obtaining a plurality of data records for a plurality of patients, each data record comprising personal health information including observable characteristics for a patient in the plurality of patients, each patient in the plurality of patients diagnosed as having a disease in a plurality of diseases;

assigning a nodal address to each data record in the plurality of data records based on the information regarding the observable characteristics for the patient, each nodal address representing a different combination of values of preselected classification variables comprising observable characteristics pertinent to a disease in the plurality of diseases for patients in the plurality of patients diagnosed with the disease, where the preselected classification variables included in the nodal address were preselected based on relevance to the disease, wherein the nodal address is effective to assign like patients diagnosed with the same disease and having the same combination of values of classification variables comprising the observable characteristics pertinent to the disease to the same nodal address, and wherein for at least some nodal addresses, the nodal address is assigned to more than one data record;

applying at least one nodal address to at least some of the plurality of data records to determine a clinically relevant set of data records, wherein a number of data records assigned the at least one nodal address is large enough for a statistically significant analysis of the clinically relevant set of data records;

analyzing the clinically relevant set of data records comprising tracking one or more clinical outcomes of one or more patients in the clinically relevant set of data records; and transmitting an electronic communication to a user device based on the analyzing to effect treatment of at least one of the one or more patients or to reduce treatment variability among the one or more patients.

2. The method as recited in claim 1, further comprising:

receiving, from a client device operated by a user, information regarding or a selection of one or more parameters for sorting the plurality of data records regarding the plurality of patients; and sorting the plurality of data records based on the one or more parameters prior to applying the one or more nodal addresses to determine the clinically relevant set of data records or sorting the clinically relevant set of data records based on the one or more parameters after applying the at least one nodal address, wherein the one or more parameters for sorting comprise at least one of sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care.

3. The method as recited in claim 1, wherein the nodal address is represented as a plurality of strings of digits, each string of digits representing a value for one of the preselected classification variables.

4. The method as recited in claim 3, wherein the preselected classification variables include a disease-specific clinical molecular phenotype, and wherein a string of digits representing a value of the disease-specific clinical molecular phenotype is determined based on a directed graph.

5. The method as recited in claim 1, wherein each nodal address is associated with one or more bundles of predetermined patient care services including at least one treatment plan for treatment of the disease associated with the nodal address; and
   wherein the method further comprises transmitting or displaying information regarding the one or more bundles of predetermined patient care services associated with the nodal address of the at least one of the one or more patients.

6. The method as recited in claim 5, wherein each of the one or more bundles of predetermined patient care services has an associated estimated predetermined cost, and the method further comprises providing a user with information regarding the estimated predetermined cost associated with at least one of the one or more bundles of predetermined patient care services associated with the nodal address of the at least one of the one or more patients.

7. The method as recited in claim 1, wherein the analyzing further comprises:
   updating records of the one or more patients whose clinical outcomes are tracked with results of the clinical outcome tracking.

8. The method as recited in claim 1, wherein the one or more clinical outcomes tracked comprise at least one of survival, response metrics, quality of life metrics, incidence of drug toxicity, severity of drug toxicity, delivered dose intensity, drugs received, drug interval, drug duration, cost of care, and death.

9. The method as recited in claim 1, wherein the analyzing further comprises:
   comparing tracked clinical outcomes between patients in the clinically relevant set of patient medical records.

10. The method as recited in claim 1, wherein the analyzing further comprises:
    identifying a specific patient as a candidate for a specific drug based, at least in part, on the tracking.

11. The method as recited in claim 1, wherein the analyzing further comprises:
    comparing clinical outcomes between patients in the clinically relevant set of data records based on treatment, cost, or a combination thereof.

12. The method as recited in claim 1, wherein the tracking clinical one or more outcomes comprises one or more of:
    (a) tracking an effect of therapy on quality of life by comparing Eastern Cooperative Oncology Group (ECOG) performance status at start of therapy, with ECOG during and/or after therapy; or
    (b) tracking diagnosis and each subsequent disease progression; or
    (c) tracking a diagnosis date, a treatment start date, and a treatment end date; or
    (e) tracking toxicity of a drug treatment and parameters of the treatment including whether the treatment was discontinued, whether the treatment was continued, whether the treatment was left unchanged, drug dosage change, number of delays in treatment, number of changes in drugs, and/or number of reductions in drugs.

13. The method as recited in claim 1, wherein transmitting an electronic communication comprises one or more of:
    sending at least a portion of the analyzed set of clinically relevant data records to a client device for display; or
    sending the electronic communication in the form of an alert to the user in response to a trigger.

14. The method as recited in claim 13, wherein
    the trigger comprises one or more of diagnosis, progression, dose change, drug change, toxicity, trending towards variance from a desired outcome for the at least one of the one or more patients, and a specific time.

15. The method as recited in claim 1, wherein analyzing the clinically relevant set of data records further comprises:
    comparing clinical outcome performance of a medical professional treating a disease to clinical outcome performance of an aggregate of medical professionals treating the disease.

16. The method as recited in claim 1, wherein the method reduces biological variability of clinical outcome for the one or more patients.

17. The method as recited in claim 1, further comprising:
    receiving an input from a user.

18. The method as recited in claim 17, further comprising:
    determining the at least one nodal address to apply to the at least some of the plurality of data records based on the input from the user; or
    determining which of the plurality of data records to which the at least one nodal address is applied based on the input from the user.

19. The method as recited in claim 18, wherein the user input identifies a particular patient in the plurality of medical records and a nodal address assigned to the particular patient is the at least one nodal address applied to the at least some of the plurality of data records to determine the clinically relevant set of data records.

20. The method as recited in claim 18, wherein the user input identifies values of at least some of the preselected classification variables to determine the at least one nodal address to apply to at least some of the plurality of data records to determine the clinically relevant set of data records.

21. The method as recited in claim 17, wherein the user input comprises a selection of or information regarding a value for one or more of sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care.

22. The method as recited in claim 17, wherein the user input identifies a health care provider and the analysis includes comparing tracked clinical outcomes for patients treated by the health care provided with clinical outcomes for patients treated by other health care providers or with clinical outcomes for patients treated by all health care providers to reduce treatment variability of clinical outcome performance.

23. The method as recited in claim 17, wherein the user input identifies which clinical outcomes are tracked.

24. The method as recited in claim 1, wherein the communication transmitted to the user device identifies the at least one of the one or more patients as a candidate for treatment with a specific drug.

25. The method as recited in claim 1, wherein the communication transmitted to the user device identifies the at least one of the one or more patients as a candidate for a clinical trial.

26. The method as recited in claim 1, wherein the analysis further comprises, based on the tracking of the one or more clinical outcomes of the one or more patients in the clinically relevant set of data records, determining whether a specific doctor associated with a tracked patient is treating the patient in accordance with treatment techniques of other doctors treating other patients in the clinically relevant set of data records.

27. The method of claim 1, wherein the analysis further comprises determining a patient survival rate for the at least one of the one or more patients based on a survival rate in the clinically relevant set of data records.

28. The method of claim 1, wherein the analysis further comprises comparing clinical outcome performance of a medical professional treating at least one of the patients in the clinically relevant set of data records with clinical outcome performance of an aggregate of medical professionals treating patents in the clinically relevant set of data records.

29. The method of claim 1, further comprising displaying results of the outcome tracking to a user in a graphical user interface.

30. A system for clinical outcome tracking and analysis comprising:
at least one processor;
storage storing a plurality of data records for a plurality of patients, each data record comprising personal health information including observable characteristics for a patient in the plurality of patients, each patient in the plurality of patients diagnosed as having a disease in a plurality of diseases;
a memory to store computer program instructions, the computer program instructions when executed on the at least one processor cause the at least one processor to perform operations comprising:
assigning a nodal address to each data record in the plurality of data records based on the information regarding the observable characteristics for the patient, each nodal address representing a different combination of values of preselected classification variables comprising observable characteristics pertinent to a disease in the plurality of diseases for patients in the plurality of patients diagnosed with the disease, where the preselected classification variables included in the nodal address were preselected based on relevance to the disease, wherein the nodal address is effective to assign like patients diagnosed with the same disease and having the same combination of values of classification variables comprising the observable characteristics pertinent to the disease to the same nodal address, and wherein for at least some nodal addresses, the nodal address is assigned to more than one data record;
applying at least one nodal address to at least some of the plurality of data records to determine a clinically relevant set of data records, wherein a number of data records assigned the at least one nodal address is large enough for a statistically significant analysis of the clinically relevant set of data records;
analyzing the clinically relevant set of data records comprising tracking one or more clinical outcomes of one or more patients in the clinically relevant set of data records; and
transmitting an electronic communication to a user device based on the analyzing to effect treatment of at least one of the one or more patients or to reduce treatment variability among the one or more patients.

31. The system as recited in claim 30, the operations further comprising:
receiving, from a client device operated by a user, information regarding or a selection of one or more parameters for sorting the plurality of data records regarding the plurality of patients; and
sorting the plurality of data records based on the one or more parameters prior to applying the one or more nodal addresses to determine the clinically relevant set of data records or sorting the clinically relevant set of data records based on the one or more parameters after applying the at least one nodal address, wherein the one or more parameters for sorting comprise at least one of sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers and cost of care.

32. The system as recited in claim 30, wherein the nodal address is represented as a plurality of strings of digits, each string of digits representing a value for one of the one or more preselected classification variables.

33. The system as recited in claim 32, wherein the preselected classification variables include a disease-specific clinical molecular phenotype, and wherein a string of digits representing a value of the disease-specific clinical molecular phenotype is determined based on a directed graph.

34. The system as recited in claim 30, wherein each nodal address is associated with one or more bundles of predetermined patient care services including at least one treatment plan for treatment of the disease associated with the nodal address; and
wherein the operations further comprise transmitting or displaying information regarding the one or more bundles of predetermined patient care services associated with the nodal address of the at least one of the one or more patients.

35. A computer readable medium storing computer program instructions for clinical outcome tracking and analysis which, when executed on at least one processor, cause the at least one processor to perform operations comprising:
accessing or obtaining a plurality of data records for a plurality of patients, each data record comprising personal health information including observable characteristics for a patient in the plurality of patients, each patient in the plurality of patients diagnosed as having a disease in a plurality of diseases;
assigning a nodal address to each data record in the plurality of data records based on the information regarding the observable characteristics for the patient, each nodal address representing a different combination of values of preselected classification variables comprising observable characteristics pertinent to a disease in the plurality of diseases for patients in the plurality of patients diagnosed with the disease, where the preselected classification variables included in the nodal address were preselected based on relevance to the disease, wherein the nodal address is effective to assign like patients diagnosed with the same disease and having the same combination of values of classification variables comprising the observable characteristics pertinent to the disease to the same nodal address, and wherein for at least some nodal addresses, the nodal address is assigned to more than one data record;

applying at least one nodal address to at least some of the plurality of records to determine a clinically relevant set of data records, wherein a number of data records assigned the at least one nodal address is large enough for a statistically significant analysis of the clinically relevant set of data records;

analyzing the clinically relevant set of data records comprising tracking one or more clinical outcomes of one or more patients in the clinically relevant set of data records; and transmitting an electronic communication to a user device based on the analyzing to effect treatment of at least one of the one or more patients or to reduce treatment variability among the one or more patients.

36. The computer readable medium as recited in claim 35, the operations further comprising:

receiving, from a client device operated by a user, information regarding or a selection of one or more parameters for sorting the plurality of data records regarding the plurality of patients; and sorting the plurality of data records based on the one or more parameters prior to applying the one or more nodal addresses to determine the clinically relevant set of data records or sorting the clinically relevant set of data records based on the one or more parameters after applying the at least one nodal address, wherein the one or more parameters comprise at least one of sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers and cost of care.

37. The computer readable medium as recited in claim 35, wherein analyzing the clinically relevant set of data records further comprises one or more of:

(a) updating records of the one or more patients whose clinical outcomes are tracked with results of the clinical outcome tracking;

(b) comparing clinical outcomes between patients in the clinically relevant set of patient medical records based on treatment, cost, or a combination of both;

(c) comparing tracked clinical outcomes between patients in the clinically relevant set of patient medical records;

(d) identifying a specific patient in the clinically relevant set of patient medical records as a candidate for a specific drug based, at least in part, on the tracking;

(e) tracking an effect of therapy on quality of life by comparing Eastern Cooperative Oncology Group (ECOG) performance status at start of therapy, with ECOG during and/or after therapy;

(f) tracking diagnosis and each subsequent disease progression;

(g) tracking a diagnosis date, a treatment start date, and a treatment end date; and (h) tracking toxicity of a drug treatment and parameters of the treatment including whether the treatment was discontinued, whether the treatment was continued, whether the treatment was left unchanged, drug dosage change, number of delays in treatment, number of changes in drugs, and/or number of reductions in drugs.

38. The computer readable medium as recited in claim 35, wherein the one or more clinical outcomes comprise at least one of survival, response metrics, quality of life metrics, incidence of drug toxicity, severity of drug toxicity, delivered dose intensity, drugs received, drug interval, drug duration, cost of care, and death.

39. The computer readable medium as recited in claim 35, wherein transmitting a communication comprises:

sending at least a portion of the analyzed set of clinically relevant data records to a client device for display; or sending the communication in the form of an alert to the user device in response to a trigger.

40. The computer readable medium as recited in claim 39, wherein the trigger comprises at least one of diagnosis, progression, dose change, drug change, toxicity, trending towards variance from a desired outcome, and a specific time.

41. A method for analysis of clinical outcomes or treatment comprising:

accessing or obtaining a plurality of data records for a plurality of patients, each data record comprising personal health information including observable characteristics for a patient in the plurality of patients, each patient in the plurality of patients diagnosed as having a disease in a plurality of diseases;

assigning a nodal address to each data record in the plurality of data records based on the information regarding the observable characteristics for the patient, each nodal address representing a different combination of values of preselected classification variables comprising observable characteristics pertinent to a disease in the plurality of diseases for patients in the plurality of patients diagnosed with the disease, where the preselected classification variables included in the nodal address were preselected based on relevance to the disease, wherein the nodal address is effective to assign like patients diagnosed with the same disease and having the same combination of values of classification variables comprising the observable characteristics pertinent to the disease to the same nodal address, and wherein for at least some nodal addresses, the nodal address is assigned to more than one data record;

applying at least one first nodal address to at least some of the plurality of data records to determine a first clinically relevant set of data records;

analyzing the first clinically relevant set of data records comprising comparing treatment or clinical outcome between patients to identify one or more outliers in patient treatment or clinical outcome in the first clinically relevant set of data records; and where at least one outlier is identified, transmitting a communication to a user device based on the analyzing to effect treatment of at least one of the outliers or to reduce treatment variability among the clinically relevant patients.

42. The method as recited in claim 41, further comprising:

applying at least one second nodal address to at least some of the plurality of data records to determine a second clinically relevant set of data records; and analyzing the second clinically relevant set of data records comprising comparing treatment or clinical outcome between patients to identify one or more outliers in patient treatment or clinical outcome in the second clinically relevant set of data records.

43. The method as recited in claim 41, further comprising:
for each nodal address other than the first nodal address that is assigned to a statistically significant number of data records in the plurality of data records:
applying the nodal address to at least some of the plurality of data records to determine a clinically relevant set of data records for the nodal address; and
analyzing the clinically relevant set of data records for the nodal address comprising comparing treatment or clinical outcome between patients to identify one or more outliers in patient treatment or clinical outcome for the nodal address.

* * * * *